(12) United States Patent
Dohi

(10) Patent No.: US 8,941,505 B2
(45) Date of Patent: Jan. 27, 2015

(54) SMOKE DETECTOR

(75) Inventor: Manabu Dohi, Gillingham (GB)

(73) Assignee: Hochiki Corporation, Tokyo (JP)

( * ) Notice: Subject to any disclaimer, the term of this patent is extended or adjusted under 35 U.S.C. 154(b) by 842 days.

(21) Appl. No.: 13/122,940

(22) PCT Filed: Oct. 9, 2009

(86) PCT No.: PCT/JP2009/005303
§ 371 (c)(1),
(2), (4) Date: Apr. 6, 2011

(87) PCT Pub. No.: WO2010/041476
PCT Pub. Date: Apr. 15, 2010

(65) Prior Publication Data
US 2011/0194111 A1    Aug. 11, 2011

(30) Foreign Application Priority Data
Oct. 9, 2008    (JP) ................. 2008-262608

(51) Int. Cl.
*G08B 17/00*    (2006.01)
*G08B 29/18*    (2006.01)
*G01N 21/53*    (2006.01)
*G08B 17/107*    (2006.01)

(52) U.S. Cl.
CPC ............. *G01N 21/53* (2013.01); *G08B 29/18* (2013.01); *G08B 17/107* (2013.01)
USPC ........................ 340/630; 340/628; 250/573

(58) Field of Classification Search
CPC ...... G08B 17/00; G08B 17/12; G08B 17/125; G08B 13/1427; G08B 17/103; G08B 17/11; G08B 17/117; H05B 1/00
USPC .......... 340/628, 630, 577, 578; 250/573, 574, 250/575
See application file for complete search history.

(56) References Cited

U.S. PATENT DOCUMENTS

| | | | |
|---|---|---|---|
| 6,239,710 B1 * | 5/2001 | Oppelt ..................... | 340/630 |
| 6,515,589 B2 * | 2/2003 | Schneider et al. ........ | 340/630 |
| 7,978,087 B2 * | 7/2011 | Siber et al. .............. | 340/630 |
| 8,243,278 B2 * | 8/2012 | Valois ..................... | 356/448 |

(Continued)

FOREIGN PATENT DOCUMENTS

| | | |
|---|---|---|
| CN | 1489756 A | 4/2004 |
| CN | 1902669 | 1/2007 |

(Continued)

OTHER PUBLICATIONS

First Office Action issued in Chinese Patent Application No. 200980138873.6; Nov. 5, 2012; 11 Pages; Chinese Patent Office.

(Continued)

*Primary Examiner* — George Bugg
*Assistant Examiner* — Edny Labbees
(74) *Attorney, Agent, or Firm* — Wood, Herron & Evans, LLP

(57) ABSTRACT

This smoke detector is provided with: a plurality of light emitting devices which emit light beams of mutually different wavelengths; and a plurality of scattered light receiving sections which receive, at a different scattering angle for each light beam of the respective wavelengths, scattered light generated due to the plurality of light beams emitted simultaneously from these light emitting devices impinging on smoke.

17 Claims, 20 Drawing Sheets

(56) References Cited

U.S. PATENT DOCUMENTS

| | | | |
|---|---|---|---|
| 8,432,062 B2 * | 4/2013 | Greene et al. | 307/18 |
| 2002/0060632 A1 * | 5/2002 | Kadwell et al. | 340/628 |
| 2002/0153499 A1 * | 10/2002 | Oppelt et al. | 250/559.16 |
| 2008/0258925 A1 * | 10/2008 | Siber et al. | 340/630 |
| 2009/0244280 A1 * | 10/2009 | Hanses et al. | 348/143 |
| 2011/0037971 A1 * | 2/2011 | Loepfe et al. | 356/51 |
| 2013/0169430 A1 * | 7/2013 | Shook | 340/539.1 |

FOREIGN PATENT DOCUMENTS

| | | | |
|---|---|---|---|
| JP | 53-114475 | | 10/1978 |
| JP | 06-109631 | | 4/1994 |
| JP | 06109631 A | * | 4/1994 |
| JP | 08-115479 | | 5/1996 |
| JP | 11-023458 | | 1/1999 |
| JP | 2000105185 | | 4/2000 |
| JP | 2005-530257 | | 10/2005 |
| JP | 2006-526211 | | 11/2006 |
| WO | 2005048208 A1 | | 5/2005 |

OTHER PUBLICATIONS

International Search Report issued in PCT Application No. PCT/JP2009/005303, mailed Jan. 12, 2010.

Japanese Patent Office, Notice of Reasons for Rejection issued in corresponding Japanese Patent Application No. 2013-151146 and English-language translation (Apr. 1, 2014) (4 pages).

The Republic of China Patent Office, Third Office Action issued in corresponding Chinese Patent Application No. 200980138873.6 and English-language translation issued on Sep. 29, 2014 (12 pages).

* cited by examiner

FIG. 5A

| | COTTON WICK (PARTICLE DIAMETER - SMALL) | | |
|---|---|---|---|
| LIGHT EMISSION CURRENT | LIGHT EMISSION CURRENT - SAME | BLUE LED CURRENT REDUCTION | INFRARED LED CURRENT REDUCTION |
| LONG WAVELENGTH LIGHT RECEPTION AMOUNT PD 1 | SMALL | SMALL | SMALL |
| SHORT WAVELENGTH LIGHT RECEPTION AMOUNT PD 2 | LARGE | SMALL (VARYING) | LARGE |
| OUTPUT RATIO PD 1 / PD 2 | Ra < 1 | Rb ≥ 1 | Rb < 1 |

FIG. 5B

| | FILTER PAPER/WATER VAPOR (PARTICLE DIAMETER - LARGE) | | |
|---|---|---|---|
| LIGHT EMISSION CURRENT | LIGHT EMISSION CURRENT - SAME | BLUE LED CURRENT - REDUCED | INFRARED LED CURRENT REDUCED |
| LONG WAVELENGTH LIGHT RECEPTION AMOUNT PD 1 | LARGE | LARGE | SMALL (VARYING) |
| SHORT WAVELENGTH LIGHT RECEPTION AMOUNT PD 2 | SMALL | SMALL | SMALL |
| OUTPUT RATIO PD 1 / PD 2 | Ra ≥ 1 | Rb ≥ 1 | Rb < 1 |

FIG. 12

| LIGHT EMITTING DEVICE DISPLACEMENT ANGLE α | 0° | 30° | 60° |
|---|---|---|---|
| FILTER PAPER OUTPUT RATIO PD 2 / PD 1 | 0.1 | 0.10 | 0.12 |
| COTTON WICK OUTPUT RATIO PD 2 / PD 1 | 0.2 | 0.26 | 0.44 |
| FILTER PAPER : COTTON WICK | 1 : 2 | 1 : 2.6 | 1 : 3.7 |

SMOKE DETECTOR

TECHNICAL FIELD

The present invention relates to a smoke detector which, based on scattered light of smoke created with light beams of two different wavelengths, determines the type of this smoke.

Priority is claimed on Japanese Patent Application No. 2008-262608, filed Oct. 9, 2008, the contents of which are incorporated herein by reference.

BACKGROUND ART

As a conventional smoke detector which detects the type of smoke, there is a smoke detector which uses a light projection device which emits light beams of a relatively long wavelength, and another light projection device which emits light beams of a relatively short wavelength.

In this type of smoke detector, the above respective light projection devices alternately emit light beams at different timings, a light receiving device receives scattered light generated due to the light beams from these light projection devices impinging on smoke particles, light reception signals output from this light receiving device are obtained separately for each light projection device, and further, a calculation is performed based on these light reception signals, to thereby determine the type of the smoke.

PRIOR ART DOCUMENTS

Patent Documents

[Patent Document 1] Japanese Unexamined Patent Application, First Publication No. H11-023458

DISCLOSURE OF INVENTION

Problems to be Solved by the Invention

However, in a smoke type determination method which uses this type of conventional smoke detector, an infrared LED and a blue LED are driven to perform light emission at mutually different timings, and meanwhile smoke is flowing at every moment. Therefore, it is impossible to obtain light reception signals with respect to exactly the same smoke, and it is difficult to accurately determine the type of smoke.

In order to compensate for this problem, it is considered to correct light receiving signals obtained at different timings so as to become light reception signals obtained at the same timing. However, for this to be achieved, there is a new problem in that a complex correction calculation needs to be performed.

The present invention takes into consideration the above circumstances, with an object of providing a smoke detector capable of accurately determining the type of smoke based on scattered light of smoke created by light beams of two wavelengths.

Means for Solving the Problem

In order to solve the above problems and achieve the object, the present invention employs following measures.

(1) A smoke detector of the present invention is provided with: a plurality of light emitting devices which emit light beams of mutually different wavelengths; and a plurality of scattered light receiving sections which receive, at a different scattering angle for each light beam of the respective wavelengths, scattered light generated due to the plurality of light beams emitted simultaneously from these light emitting devices impinging on smoke.

(2) In the smoke detector according to (1) above, at the time of driving the respective light emitting devices to simultaneously perform light emission, the driving conditions may be of at least two different types for each of the light emitting devices at a predetermined timing.

(3) In the smoke detector according to (1) above, the presence or absence, or type of the smoke may be determined based on a correlation between respective light reception signals from each of the scattered light receiving sections.

(4) In the smoke detector according to either one of (1) and (2) above, the presence or absence, or type of the smoke may be determined based on a correlation between the driving condition of each of the light emitting devices and light reception signals of each of the light receiving sections under this driving condition.

(5) Another smoke detector of the present invention is provided with: a first scattered light detection section in which a long wavelength light emitting device which emits a first light beam having a predetermined long wavelength, and a long wavelength light receiving device which receives first scattered light generated due to the first light beam emitted from this long wavelength light emitting device impinging on smoke, are arranged with a first scattering angle; a second scattered light detection section in which a short wavelength light emitting device which emits a second light beam having a predetermined short wavelength, and a short wavelength light receiving device which receives second scattered light generated due to the second light beam emitted from this short wavelength light emitting device impinging on smoke, are arranged with a second scattering angle, which differs from the first scattering angle; a light emission control section which makes the long wavelength light emitting device and the short wavelength light emitting device simultaneously perform light emission; a first detection processing section which obtains a first long wavelength light reception signal from the long wavelength light receiving device, and a first short wavelength light reception signal from the short wavelength light receiving device; and a second detection processing section which obtains a second long wavelength light reception signal from the long wavelength light receiving device, and a second short wavelength light reception signal from the short wavelength light receiving device.

(6) In the smoke detector according to (5) above, the light emission control section may be provided with a driving current variable control section which changes a driving current of either one of the long wavelength light emitting device and the short wavelength light emitting device.

(7) In the smoke detector according to either one of (5) and (6) above, there may be further provided a smoke type determination section which determines the type of the smoke based on the first long wavelength light reception signal, the second long wavelength light reception signal, the first short wavelength light reception signal, and the second short wavelength light reception signal.

(8) In the case of the smoke detector according to (7) above, there may be employed a configuration in which: the light emission control section drives the long wavelength light emitting device and the short wavelength light emitting device to simultaneously perform light emission with the same light emission current; the first detection processing section obtains the first long wavelength light reception signal from the long wavelength light receiving device and the first short wavelength light reception signal from the short wavelength light receiving device; the light emission control section changes the light emission current of either one of the long wavelength light emitting device and the short wavelength light emitting device, and then makes them emit light simultaneously; the second detection processing section obtains the second long wavelength light reception signal from the long wavelength light receiving device and the second short wavelength light reception signal from the short wavelength light receiving device; and the smoke type determination section determines the diameter of particles of the smoke as being greater than a predetermined value if a proportion of a long wavelength light reception signal is relatively higher, and on the other hand, it determines the diameter of the particles of the smoke as being smaller than the predetermined value if a proportion of a short wavelength light reception signal is relatively higher, based on the first long wavelength light reception signal, the second long wavelength light reception signal, the first short wavelength light reception signal, and the second short wavelength light reception signal.

(9) In the smoke detector according to (7) above, there may be employed a configuration in which: having made the light emission current to be flowed to the short wavelength light emitting device lower than the light emission current to be flowed to the long wavelength light emitting device, the light emission control section makes them perform simultaneous light emission; the second detection processing section obtains the second long wavelength light reception signal from the long wavelength light receiving device, and the second short wavelength light reception signal from the short wavelength light receiving device; and the smoke type determination section (i) finds a first output ratio, which is found by dividing the first long wavelength light reception signal by the second short wavelength light reception signal, (ii) it estimates the diameter of the particles of the smoke as being smaller than a predetermined value if the first output ratio is less than 1, (iii) having established this estimation, it finds a second output ratio, which is found by dividing the second long wavelength light reception signal by the second short wavelength light reception signal, and then (iv) it determines the result of the estimation as being correct if this second output ratio is 1 or higher.

(10) In the smoke detector according to (7) above, there may be employed a configuration in which: having made the light emission current to be flowed to the short wavelength light emitting device lower than the light emission current to be flowed to the long wavelength light emitting device, the light emission control section makes them perform simultaneous light emission; the second detection processing section obtains the second long wavelength light reception signal from the long wavelength light receiving device, and the second short wavelength light reception signal from the short wavelength light receiving device; and the smoke type determination section (i) finds a first output ratio, which is found by dividing the first long wavelength light reception signal by the first short wavelength light reception signal, (ii) it estimates the diameter of the particles of the smoke as being greater than a predetermined value if this first output ratio is 1 or higher, (iii) having established this estimation, it finds a second output ratio, which is found by dividing the second long wavelength light reception signal by the second short wavelength light reception signal, and then (iv) it determines the result of the estimation as being correct if this second output ratio is 1 or higher.

(11) In the smoke detector according to (7) above, there may be employed a configuration in which: having made the light emission current to be flowed to the long wavelength light emitting device lower than the light emission current to be flowed to the short wavelength light emitting device, the light emission control section makes them perform simultaneous light emission; the second detection processing section obtains the second long wavelength light reception signal from the long wavelength light receiving device, and the second short wavelength light reception signal from the short wavelength light receiving device; and the smoke type determination section (i) finds a first output ratio, which is found by dividing the first long wavelength light reception signal by the first short wavelength light reception signal, (ii) it estimates the diameter of the particles of the smoke as being smaller than a predetermined value if this first output ratio is 1 or higher, (iii) having established this estimation, it finds a second output ratio, which is found by dividing the second long wavelength light reception signal by the second short wavelength light reception signal, and then (iv) it determines the result of the estimation as being correct if this second output ratio is less than 1.

(12) In the smoke detector according to (7) above, there may be employed a configuration in which: having made the light emission current to be flowed to the long wavelength light emitting device lower than the light emission current to be flowed to the short wavelength light emitting device, the light emission control section makes them perform simultaneous light emission; the second detection processing section obtains the second long wavelength light reception signal from the long wavelength light receiving device, and the second short wavelength light reception signal from the short wavelength light receiving device; and the smoke type determination section (i) finds a first output ratio, which is found by dividing the first long wavelength light reception signal by the second short wavelength light reception signal, (ii) it estimates the diameter of the particles of the smoke as being greater than a predetermined value if this first output ratio is 1 or higher, (iii) having established this estimation, it finds a second output ratio, which is found by dividing the second long wavelength light reception signal by the second short wavelength light reception signal, and then (iv) it determines the result of the estimation as being correct if this second output ratio is less than 1.

(13) In the smoke detector according to (7) above, there may be employed a configuration in which: having made the light emission current to be flowed to the short wavelength light emitting device lower than the light emission current to be flowed to the long wavelength light emitting device, the light emission control section makes them perform the simultaneous light emission; the second detection processing section obtains the second long wavelength light reception signal from the long wavelength light receiving device and the second short wavelength light reception signal from the short wavelength light receiving device; and the smoke type determination section (i) finds a first output ratio, which is found by dividing the first long wavelength light reception signal by the second short wavelength light reception signal, and a second output ratio, which is found by dividing the second long wavelength light reception signal by the second short wavelength light reception signal, and (ii) it determines the diameter of the particles of the smoke as being smaller than a predetermined value if the rate of change from the first output ratio to the second output ratio is greater than or equal to a predetermined threshold value, and on the other hand, it determines the diameter of the particles of the smoke as being greater than the predetermined value if the rate of change is less than the threshold value.

(14) In the smoke detector according to (7) above, there may be employed a configuration in which: having made the light emission current to be flowed to the long wavelength light emitting device lower than the light emission current to be flowed to the short wavelength light emitting device, the light emission control section makes them perform the simultaneous light emission; the second detection processing section obtains the second long wavelength light reception signal from the long wavelength light receiving device and the second short wavelength light reception signal from the short wavelength light receiving device; and the smoke type determination section (i) finds a first output ratio, which is found by dividing the first long wavelength light reception signal by the second short wavelength light reception signal, and a second output ratio, which is found by dividing the second long wavelength light reception signal by the second short wavelength light reception signal, and (ii) it determines the diameter of the particles of the smoke as being smaller than a predetermined value if the rate of change from the first output ratio to the second output ratio is less than a predetermined threshold value, and on the other hand, it determines the diameter of the particles of the smoke as being greater than the predetermined value if the rate of change is greater than or equal to the threshold value.

(15) Still another smoke detector of the present invention is provided with: a first scattered light detection section in which a long wavelength light emitting device which emits a first light beam having a predetermined long wavelength, and a long wavelength light receiving device which receives first scattered light generated due to the first light beam emitted from this long wavelength light emitting device impinging on smoke, are arranged with a first scattering angle; a second scattered light detection section in which a short wavelength light emitting device which emits a second light beam having a predetermined short wavelength which is shorter than the long wavelength, and a short wavelength light receiving device which receives second scattered light generated due to the second light beam emitted from this short wavelength light emitting device impinging on smoke, are arranged with a second scattering angle, which differs from the first scattering angle; a light emission control section which makes the long wavelength light emitting device and the short wavelength light emitting device to simultaneously perform light emission with the same light emission current; a detection processing section which obtains a long wavelength light reception signal from the long wavelength light receiving device, and a short wavelength light reception signal from the short wavelength light receiving device; and a smoke type determination section which determines the type of the smoke, based on the long wavelength light reception signal and the short wavelength light reception signal.

(16) In the smoke detector according to (15) above, there may be employed a configuration in which the smoke type determination section: (i) sets a first output ratio, which is found by dividing a known long wavelength light reception signal obtained with respect to one or more types of preliminarily determined smoke by a known short wavelength light reception signal, as a threshold value; (ii) finds a second output ratio, which is found by dividing the long wavelength light reception signal obtained in the light receiving processing section with respect to unknown smoke, by the short wavelength light reception signal; and (iii) compares this second output ratio with the threshold value to thereby determined the type of the smoke.

(17) In the smoke detector according to (15) above, the position of the short wavelength light emitting device of the second scattered light detection section may be arranged so as to be horizontal-rotationally displaced about a predetermined axis, with respect to the position of the long wavelength light emitting device of the first scattered light detection section.

(18) In the smoke detector according to either one of (8) and (15) above, there may be employed a configuration in which: there is further provided a detector main body having a flat exposed surface; the long wavelength light emitting device, the long wavelength light receiving device, the short wavelength light emitting device, and the short wavelength light receiving device are respectively embedded in the exposed surface; the first light beam emitted from the long wavelength light emitting device and the second light beam emitted from the short wavelength light emitting device are irradiated into an external smoke detection space which the exposed surface faces, to thereby generate the first scattered light and the second scattered light generated due to the above light beams impinging on the smoke within the external smoke detection space; and the first scattered light is received by the long wavelength light receiving device while the second scattered light is received by the short wavelength light receiving device. Moreover, on the exposed surface, there may be mounted a translucent cover which protects the respective light emitting devices and light receiving devices embedded in this exposed surface.

Effect of The Invention

According to the smoke detector of the present invention, a light emitting device which emits a light beam of a relatively long wavelength, and a light emitting device which emits a light beam of a relatively short wavelength, are made to perform light emission at the same timing, and it is thereby possible to obtain, with respect to the same smoke, light reception signals of scattered lights created respectively by the long wavelength light beam and the short wavelength light beam. As a result, it is possible to more accurately identify the type of smoke.

Here, in a case where smoke particles are comparatively small (for example, in a case of a smoking combustion with a cotton wick), the scattered light component due to a short wavelength (for example, 470 nm) light beam of a blue LED becomes relatively greater. On the other hand, in a case of a smoking combustion due to water vapor and a filter paper where smoke particles are comparatively large, in contrast, the scattered light component due to a long wavelength (for example, 870 nm) light beam of an infrared LED becomes relatively greater.

Accordingly, based on light reception signals obtained where the light emitting device which emits a long wavelength light beam and the light emitting device which emits a short wavelength light beam are driven with the same current to simultaneously perform light emission, it is determined, for example from the output ratio of the light reception signals, whether the influence of the long wavelength light beam is greater or the influence of the short wavelength light beam is greater. However, without any changes, accurate determination may not be made in some cases. Therefore, having increased or reduced the light emission current for emitting either one of a long wavelength light beam of a short wavelength light beam, they are made to perform simultaneous light emission, and the influences of the respective long wavelength light beam and short wavelength light beam are verified again. Since it is eventually possible to determine the type of smoke based on the results of the re-verification, the type of smoke can be determined more accurately.

Moreover, in another embodiment of a smoke detector of the present invention, it is set so that the scattering angle of the short wavelength light beam becomes sufficiently greater than the scattering angle of the long wavelength light beam (so that, for example, the scattering angle of the short wavelength light beam is 90° which becomes sufficiently greater than the scattering angle 40° of the long wavelength light beam). Consequently, the degree of the influence on the scattered light component due to the long wavelength light beam and short wavelength light beam can be made high, and it is possible, without performing a re-verification, to accurately determine the type of smoke by performing only simultaneous light emission with the same light emission current. Therefore, since there is no need for conducting the re-verification, the processing load can be reduced and a determination can be made at high speed.

BRIEF DESCRIPTION OF THE DRAWINGS

FIG. 5A is an explanatory diagram showing the influence of a scattered light component of a long wavelength and the influence of a scattered light component of a short wavelength, with respect to smoke of a small particle diameter due to a smoking combustion of a cotton wick.

FIG. 5B is an explanatory diagram showing the influence of a scattered light component of a long wavelength and the influence of a scattered light component of a short wavelength, with respect to smoke of a large particle diameter such as smoke and water vapor due to a smoking combustion of a filter paper.

FIG. 12 is a table showing measurement results of output ratios according to filter papers and cotton wicks with respect to the displacement angle of the blue LED in the respective scattered light detection structures of FIG. 11A to FIG. 11C.

BEST MODE FOR CARRYING OUT THE INVENTION

Hereunder, respective embodiments of a smoke detector of the present invention are described. However, in the descriptions, the same constituents are given the same reference symbols, and overlapping descriptions thereof are omitted.

[First Embodiment]

Figure 1A:
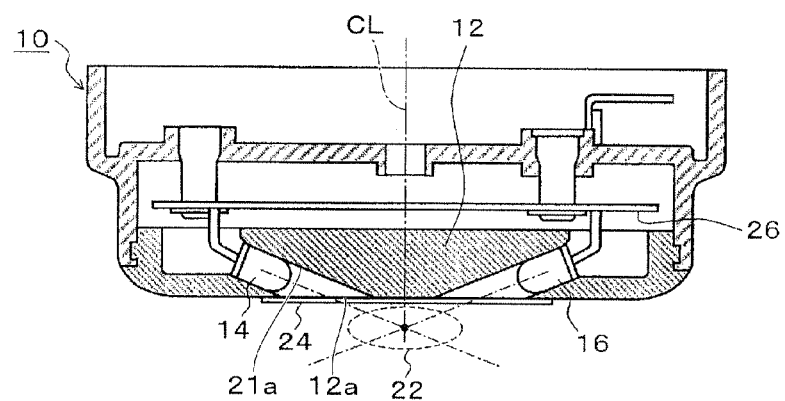
FIG. 1A is a diagram showing a first embodiment of a smoke detector of the present invention, and is an A-A cross-sectional view of FIG. 1B.
Figure 1B:
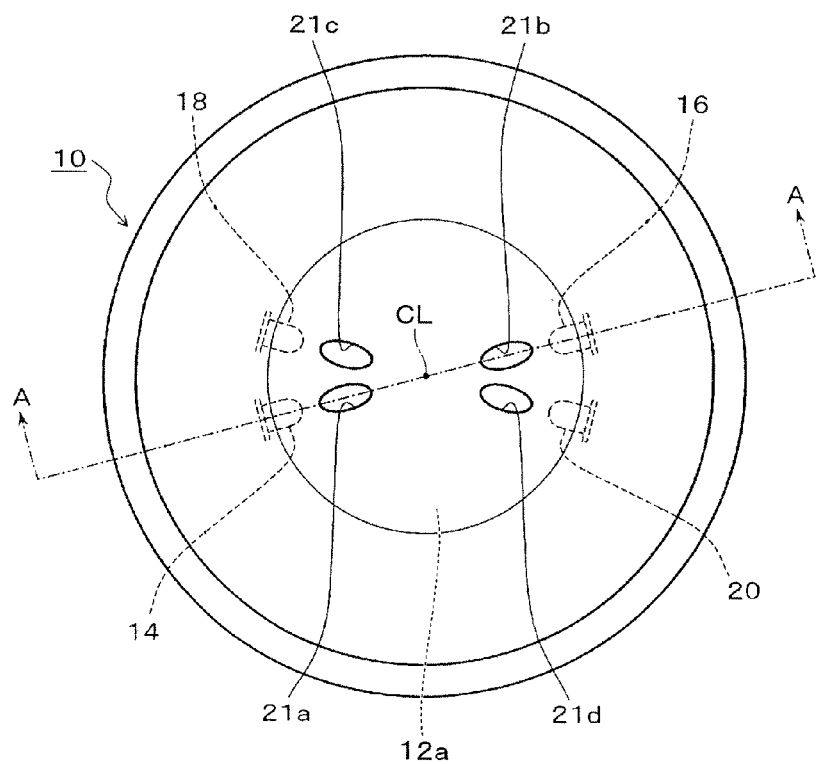
FIG. 1B is a bottom view of the same smoke detector.

FIG. 1A and FIG. 1B are diagrams showing a structure of a smoke detector according to a first embodiment of the present invention, wherein FIG. 1A shows an A-A cross-sectional view of FIG. 1B, and FIG. 1B shows a bottom view seen from the lower side.

As shown in FIG. 1A, the smoke detector of the present embodiment is a flat type smoke detector in which an exposed surface thereof is flat and a smoke detection space is to be formed outside thereof. The flat type smoke detector of the present embodiment is such that a holder 12 is housed in the lower side of the interior of a sensor main body 10. On the lower side of the holder 12, there is formed a flat exposed surface 12a. Further, in respective housing holes formed in this exposed surface 12a each having openings 21a to 21d, there are provided scattered light detection sections comprising two pairs of a light emitting device and a light receiving device.

The exposed surface 12a of the holder 12 is covered by a thin translucent cover 24. The openings 21a to 21d are thereby covered so that ingress of power dust or the like will be prevented. On the reverse side (upper side) of the holder 12, there is incorporated a circuit board 26. On this circuit board 26, there is mounted a sensor circuit for determining the presence of a fire hazard occurrence and the type of smoke, based on a scattered light type smoke detection method.

In the flat type smoke detector of the present embodiment, there are provided a first scattered light detection section which detects scattered light due to a long wavelength light beam, and a second scattered light detection section which detects scattered light due to a short wavelength light beam.

The first scattered light detection section is provided with an infrared LED 14 serving as a long wavelength light emitting device which emits a light beam of a long wavelength, for example, 870 nm, and a long wavelength light receiving device 16 using a photodiode, which receives scattered light generated due to the light emitted from this infrared LED 14 impinging on smoke. The infrared LED 14 and the long wavelength light receiving device 16 are arranged with a first scattering angle $\theta 1$ (for example, $\theta 1=40°$) therebetween.

The second scattered light detection section is provided with a blue LED 18 serving as a short wavelength light emitting device which emits a light beam of a short wavelength, for example, 470 nm, and a short wavelength light receiving device 20 which receives scattered light generated due to the light emitted from this blue LED 18 impinging on the smoke. The blue LED 18 and the short wavelength light receiving device 20 are arranged with a second scattering angle $\theta 2$ (for example, $\theta 2=50°$) therebetween, which differs from the above first scattering angle $\theta 1=40°$.

In a case of a smoking combustion of, for example, a cotton wick where the particle diameter of smoke is comparatively small, the scattered light component due to a light beam of a short wavelength, for example, 470 nm emitted from the blue LED 18 becomes relatively greater. On the other hand, in a case of a smoking combustion due to water vapor and a filter paper where smoke particles are comparatively large, in contrast, the scattered light component due to a light beam of a long wavelength, for example, 870 nm emitted from the infrared LED 14 becomes relatively greater.

Taking the first scattered light detection section as an example, detection scattered light due to smoke is performed such that first, a long wavelength light beam emitted from the infrared LED 14 provided within the holder 12 is irradiated into an external smoke detection space 22 on the lower side of the exposed surface 12a via the opening 21a and the translucent cover 24. When smoke caused by a fire hazard enters into the external smoke detection space 22, the light beam emitted from the infrared LED 14 impinges on smoke particles and becomes scattered, and this scattered light is irradiated, via the translucent cover 24 and the opening 21b, onto the long wavelength light receiving device 16 provided within the holder 12. As a result, the long wavelength light receiving device 16 outputs a light reception signal according to the received scattered light generated due to the long wavelength light beam impinging on the smoke particles.

The content of the above operation is similar to that of the second scattered light detection section provided with the blue LED 18 and the short wavelength light receiving device 20. As can be clearly understood from FIG. 1B, the first scattered light detection section and the second scattered light detection section are arranged with a displacement of a predetermined angle, so that the optical axes thereof when seen on a plane intersect with each other on the center axis CL of the exposed surface 12a.

In the flat type smoke detector of the present embodiment having the above configuration, a conventional smoke detection section having a labyrinth structure is not provided in the sensor main body 10. Instead of this, the infrared LED 14, the blue LED 18, the long wavelength light receiving device 16, and the short wavelength light receiving device 20 are embedded and housed in the holder 12, and the openings 21a to 21d are exposed to the outside via the translucent cover 24. As a result, since there is no need for providing a smoke detection section having a labyrinth structure, the height dimension of this flat type smoke detector can be made small, and consequently, a significantly thinner thickness has been achieved compared to the conventional thickness.

Figure 2:
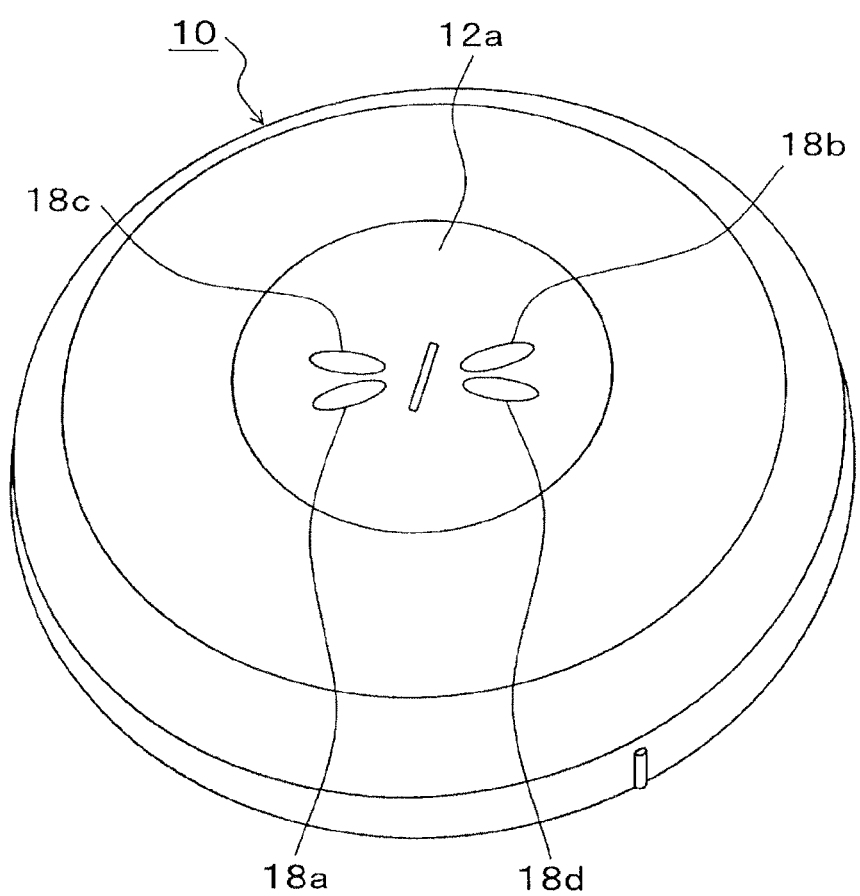
FIG. 2 is a perspective view showing an external appearance of the same smoke detector.

FIG. 2 is a perspective view showing an external appearance of the flat type smoke detector of the present embodiment. As shown in FIG. 1A to FIG. 2, the sensor main body 10 is of a smoothly curved dish-like disk shape, and in the center thereof, there is provided the flat exposed surface 12a. In this exposed surface 12a, there are formed opening end sections of the openings 21a to 21d which house the infrared LED 14, the blue LED 18, the long wavelength light receiving device 16, and the short wavelength light receiving device 20 shown in FIG. 1A and FIG. 1B.

Figure 3A:
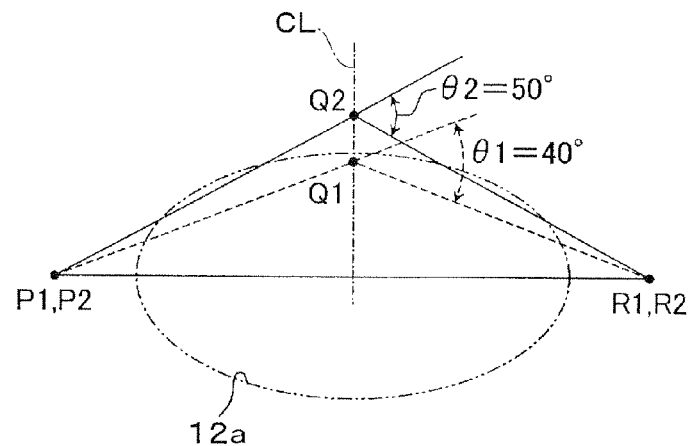
FIG. 3A is an explanatory diagram schematically showing a scattered light detection structure of the same smoke detector.
Figure 3B:
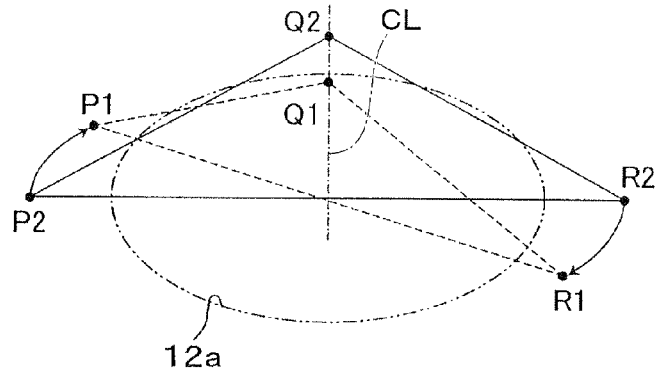
FIG. 3B is an explanatory diagram schematically showing the scattered light detection structure of the same smoke detector.

FIG. 3A and FIG. 3B are explanatory diagrams schematically showing the scattered light detection structure of the flat type smoke detector of the present embodiment. FIG. 3A shows a state where the first scattered light detection section and the second scattered light detection section are arranged overlapped on each other on a planar space parallel with the exposed surface 12a.

Here, the first scattered light detection section is shown as a triangular shape illustrated with the broken line having a light emission point P1, a detection point Q1, and a light receiving point R1. The first constituent angle $\theta 1$ serving as an angle between the extended line of the straight line connecting the light emission point P1 and the detection point Q1, and the straight line connecting the detection point Q1 and the light receiving point R1, is $\theta 1=40°$ for example.

Moreover, the second scattered light detection section is shown as a triangular shape illustrated with the solid line having a light emission point P2, a detection point Q2, and a light receiving point R2. The second scattering angle $\theta 2$ serving as an angle between the extended line of the straight line connecting the light emission point P2 and the detection point Q2, and the straight line connecting the detection point Q2 and the light receiving point R2, is $\theta 2=50°$ for example.

In the case where these first scattered light detection section and second scattered light detection section are actually arranged as shown in FIG. 1A to FIG. 2, the light emission points P1 and P2 cannot be arranged at the same position, and the light receiving points R1 and R2 cannot arranged at the same position. Therefore, as shown in FIG. 3B, they are arranged at positions horizontal-rotationally displaced (about the center axis CL) by a predetermined angle.

Figure 3C:
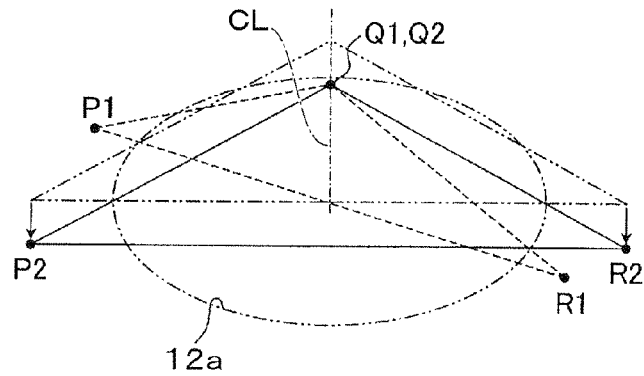
FIG. 3C is an explanatory diagram schematically showing the scattered light detection structure of the same smoke detector.

Furthermore, in order to match the detection points Q1 and Q2 of the first scattered light detection section and the second scattered light detection section, for example, as shown in FIG. 3C, by displacing in a parallel movement in the horizontal direction the bottom edge portion on the second scattered light detection section side of the solid line having the detection point Q2 positioned higher than the exposed surface 12a, from the center position (the position of the center axis CL), and further, in this state, by inclining the detection point Q2 toward the detection point Q1, the positions of the detection points Q1 and Q2 can be matched.

By matching the two detection points Q1 and Q2 in this manner, when a light beams is emitted simultaneously from the light emission points P1 and P2, it is possible that these light beams are impinged on the smoke at the same position to generate respective scattered lights, and these scattered lights can be received at the light receiving points R1 and R2.

Figure 4:
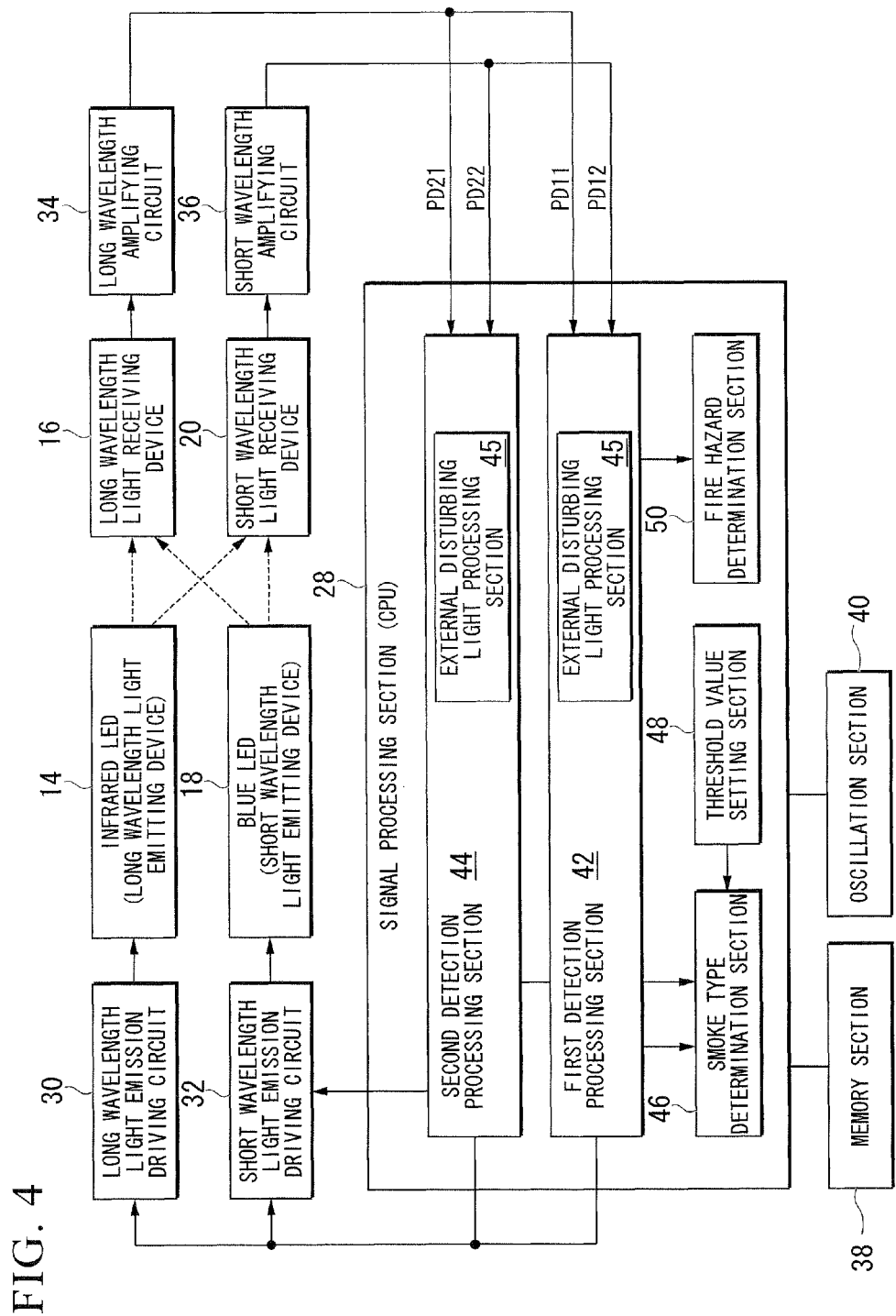
FIG. 4 is a block diagram of a sensor circuit in the same embodiment.

FIG. 4 shows a block diagram of the sensor circuit in the present embodiment. As shown in this FIG. 4, the sensor circuit of the present embodiment is provided with a signal processing section 28 which uses a CPU, a long wavelength light emission driving circuit 30, a short wavelength light emission driving circuit 32, a long wavelength amplifying circuit 34, a short wavelength amplifying circuit 36, a memory section 38, and an oscillation section 40, which are connected to the signal processing section 28.

The long wavelength light emission driving circuit 30 drives the infrared LED 14 serving as a long wavelength light emitting device to perforin light emission. The long wavelength amplifying circuit 34, when the long wavelength light receiving device 16 receives scattered light of a long wavelength caused by smoke, inputs a long wavelength light reception signal PD 11, which is transmitted from this long wavelength light receiving device 16, to the signal processing section 28.

The short wavelength light emission driving circuit 32 drives the blue LED 18 serving as a short wavelength light emitting device to perform light emission. The short wavelength amplifying circuit 36, when the short wavelength light receiving device 20 receives scattered light of a short wavelength caused by the smoke, amplifies a light reception signal, which is transmitted from this short wavelength light receiving device 20, and generates a short wavelength light reception signal PD 12, and inputs this to the signal processing section 28.

In the signal processing section 28, as functions realized by programs executed by the CPU, there are provided a first detection processing section 42, a second detection processing section 44, a smoke type determination section 46, a threshold value setting section 48, and a fire hazard determination section 50.

The first detection processing section 42 outputs light emission pulses generated based on a clock generated by the oscillation section 40, simultaneously to the long wavelength light emission driving circuit 30 and the short wavelength light emission driving circuit 32, and it thereby makes the infrared LED 14 and the blue LED 18 simultaneously emit light with a light emission current of the same current value. Light emission driving performed by the long wavelength light emission driving circuit 30 and the short wavelength light emission driving circuit 32 are intermittently performed in a one second cycle for example. Single light emission driving is performed, for example, by consecutively outputting a 3 kHz light emission pulse five times.

By having this first detection processing section 42 make the infrared LED 14 and the blue LED 18 perform simultaneous light emission with the same light emission current, the long wavelength light receiving device 16 and the short wavelength light receiving device 20 respectively receive a scattered light component generated as a result of these impinging on the smoke. A light reception signal transmitted from the long wavelength light receiving device 16 is amplified by the long wavelength amplifying circuit 34, and it is then input to the first detection processing section 42 as a long wavelength light reception signal PD 11. Moreover, a light reception signal transmitted from the short wavelength light receiving device 20 is amplified by the short wavelength amplifying circuit 36, and it is then similarly input to the first detection processing section 42 as a short wavelength light reception signal PD 12.

By using the long wavelength light reception signal PD 11 and the short wavelength light reception signal PD 12 output in the simultaneous light emission driving of the long wavelength light and short wavelength light performed by the first detection processing section 42, the smoke type determination section 46 can estimate the type of the smoke. However, since there is a possibility that the smoke type may be misestimated in a single estimating determination, in the present embodiment, the second detection processing section 44 executes a detection process for a re-verification.

That is to say, the second detection processing section 44 changes the light emission current of either one of the infrared LED 14 and the blue LED 18 so that it will be different from that of the other, and then the second detection processing section 44 makes them perform a simultaneous light emission, to obtain a long wavelength light reception signal PD 21 and a short wavelength light reception signal PD 22. In the present embodiment, the second detection processing section 44 keeps the light emission current of the infrared LED 14 unchanged, and makes the light emission current of the blue LED 18 lower than the light emission current of the infrared LED 14, and then it makes them perform simultaneous light emission, to thereby obtain the long wavelength light reception signal PD 21 and the short wavelength light reception signal PD 22 for a verification.

Based on the long wavelength light reception signal PD 11 and the short wavelength light reception signal PD 12 obtained by the first detection processing section 42, and on the long wavelength light reception signal PD 21 and the short wavelength light reception signal PD 22 obtained by the second detection processing section 44, the smoke type determination section 46 determines it as being "smoke of a large particle diameter" if the proportion of the long wavelength light reception signal is greater, and determines it as being "smoke of a small particle diameter" if the proportion of the short wavelength light reception signal is greater.

That is to say, in the smoke type determination performed by the smoke type determination section 46, an output ratio Ra, which is found by dividing the output of the long wavelength light reception signal PD 11 obtained by the first detection processing section 42 by the output of the short wavelength light reception signal PD 12, is found as being R=PD 11/PD 12. Similarly, an output ratio Rb, which is found by dividing the output of the long wavelength light reception signal PD 21 obtained by the second detection processing section 44 for example in the case where the light emission current is reduced, by the output of the short wavelength light reception signal PD 22, is found as being R=PD 11/PD 12. The smoke type is determined based on the two output ratios Ra and Rb found in this manner.

The fire hazard determination section 50 determines an occurrence of a fire hazard if at least either one of the long wavelength light reception signal PD 11 and the short wavelength light reception signal PD 12 obtained by the first detection processing section 44, exceeds a predetermined fire hazard determination threshold value, and it transmits a fire hazard detection signal to a receiver device or the like not shown in the figure.

Moreover, the flat type smoke detector of the present embodiment is made as a flat type in order to detect scattered light generated as a result of the light impinging on smoke within the external smoke detection space shown in FIG. 1A and FIG. 1B. However, in order to suppress and eliminate the influence of external disturbing light due to this employment of the flat type, an external disturbing light processing section 45 is provided respectively in the first detection processing section 42 and the second detection processing section 44. This external disturbing light processing section 45 is described later.

FIG. 5A and FIG. 5B are tables used in the determination process performed by the smoke type determination section 46 shown in FIG. 4, and show the influence of the long wavelength scattered light component and the short wavelength scattered light component with respect to the type of smoke.

FIG. 5A shows the long wavelength light reception amounts PD 1 and short wavelength light reception amounts PD 2 with respect to cotton wick combustion smoke, which is a type of smoke with a relatively small particle diameter, and the output ratio PD 1/PD 2 of these. This FIG. 5A shows a case where the light emission currents of the blue LED 18 and the infrared LED 14 are the same, a case where the light emission current of the blue LED 18 is reduced to a value lower than the light emission current of the infrared LED 14, and a case where the light emission current of the infrared LED 14 is reduced to a value lower than the light emission current of the blue LED 18.

As shown in FIG. 5A, in the case of smoke with a small particle diameter caused by smoking combustion of a cotton wick, the scattered light component (short wavelength light reception amount PD 2) due to the light beam of a short wavelength, for example, 470 nm from the blue LED 18 becomes greater. Therefore, in the case where the light emission current is the same, if the scattered light component due to the smoke caused by smoking combustion of a cotton wick becomes greater, the short wavelength light reception amount PD 12 caused by the light emission of the blue LED 18 becomes large, and the long wavelength light reception amount PD 11 caused by the light emission of the infrared LED 14 becomes small. Therefore, the output ratio Ra=PD 11/PD 12 in this case takes a value less than 1.

Next, in the case where the light emission current of the blue LED 18 is reduced and then a simultaneous light emission is performed in order to conduct a re-verification, the long wavelength light reception amount PD 1 due to the infrared LED 14 hardly changes and is the same as that in the case with the same light emission current, and on the other hand, in the short wavelength light reception amount PD 2 due to the blue LED 14, the scattered light component is reduced due to the reduction in the light amount caused by the reduction in the light emission current, and the short wavelength light reception amount PD 2 changes to a small value. As a result, the output ratio Rb=PD 21/PD 22, which was less than 1 in the case with the same light emission current, changes to a value 1 or higher because the value of the denominator side becomes smaller.

Therefore, in the case where detection results are obtained such that the output ratio Ra at the time when the infrared LED 14 and the blue LED 18 are made to perform light emission simultaneously with the same light emission current is less than 1, and the output ratio Rb at the time when the light emission current of the blue LED 18 is subsequently reduced is 1 or greater (that is to say, in the case where there is obtained a relationship of Ra<1 and Rb≥1), the smoke can be determined as being smoke with a small particle diameter caused by smoking combustion of a cotton wick or the like.

Furthermore, the light emission current of the infrared LED 14 may be reduced and then the simultaneous light emission may be performed in order to conduct a re-verification. In this case, even if the long wavelength light due to the smoke with a small particle diameter generated as a result of smoking combustion of a cotton wick is reduced, the influence thereof on the short wavelength scattered light component is small because the particle diameter is small. Consequently, both of the long wavelength light reception amount and the short wavelength light reception amount hardly change from those in the case with the same light emission current, and similarly the output ratio Rb takes a value less than 1. Therefore, in the case where the output ratio Ra with the same light emission current is less than 1, and also the output ratio Rb when light emission is simultaneously performed with the reduced light emission current of the infrared LED 14 for a re-verification is less than 1 (that is to say, in the case where Ra<1 and Rb<1), the smoke can be determined as being smoke of a small particle diameter caused by smoking combustion of a cotton wick or the like.

On the other hand, FIG. 5B shows a relationship between the long wavelength light reception amount PD 1 and the short wavelength light reception amount PD 2 with respect to smoke with a large particle diameter such as smoke caused by smoking combustion of a filter paper, and the output ratio PD 1/PD 2. In contrast, as for the smoke with a large particle diameter caused by smoking combustion of a filter paper for example, the scattered light component due to a light beam of a long wavelength, for example, 870 nm emitted from the infrared LED 14, becomes greater.

Therefore, in the case of smoke generated as a result of smoking combustion of a filter paper, there is a relationship in which the long wavelength light reception signal PD 1 obtained in the simultaneous light emission with the same light emission current is relatively large, and the short wavelength light reception signal PD 2 is relatively small, and the output ratio Ra at this time takes a value 1 or higher.

Next, in the case where, for example, the light emission current of the blue LED 18 is reduced and then a simultaneous light emission is performed in order to conduct a re-verification, with the smoke of a large particle diameter caused by smoking combustion of a filter paper, the influence on the scattered light is almost none even if the strength of the light beam of a short wavelength is reduced. Consequently, as with the case with the same light emission current, the magnitude relationship between the long wavelength light reception amount and the short wavelength light reception amount is maintained, and the output ratio Rb at this time is 1 or higher as with the case with the same light emission current.

Therefore, in the case where the output ratio Ra obtained as a result of performing simultaneous light emission with the same light emission current is 1 or higher, and also the output ratio Rb obtained as a result of reducing the light emission current of the blue LED 18 for re-verification and then performing a simultaneous light emission, is similarly 1 or higher (that is to say, in the case where there is obtained a relationship Ra≥1 and Rb≥1), the smoke can be determined as being smoke with a large particle diameter caused by smoking combustion of a filter paper or by water vapor.

Moreover, when conducting a re-verification, the light emission of the infrared LED 14 may be reduced. In this case, due to the reduction in the long wavelength light, the light receiving component of the scattered light in the long wavelength light reception signal PD 1 is reduced, and the light reception amount changes to a smaller value. Therefore, when conducting the re-verification, the output ratio Rb in this case changes from a value 1 or higher in the case with the same light emission current, to a value less than 1.

Therefore, in the case where the output ratio Ra obtained as a result of performing simultaneous light emission with the same light emission current is 1 or higher, and also the output ratio Rb obtained as a result of reducing the light emission current of the infrared LED 14 for re-verification and then performing a simultaneous light emission, is similarly 1 or higher (that is to say, in the case where there is obtained a relationship Ra≥1 and Rb<1), the smoke can be determined as being smoke with a large particle diameter caused by smoking combustion of a filter paper or the like.

Figure 6:
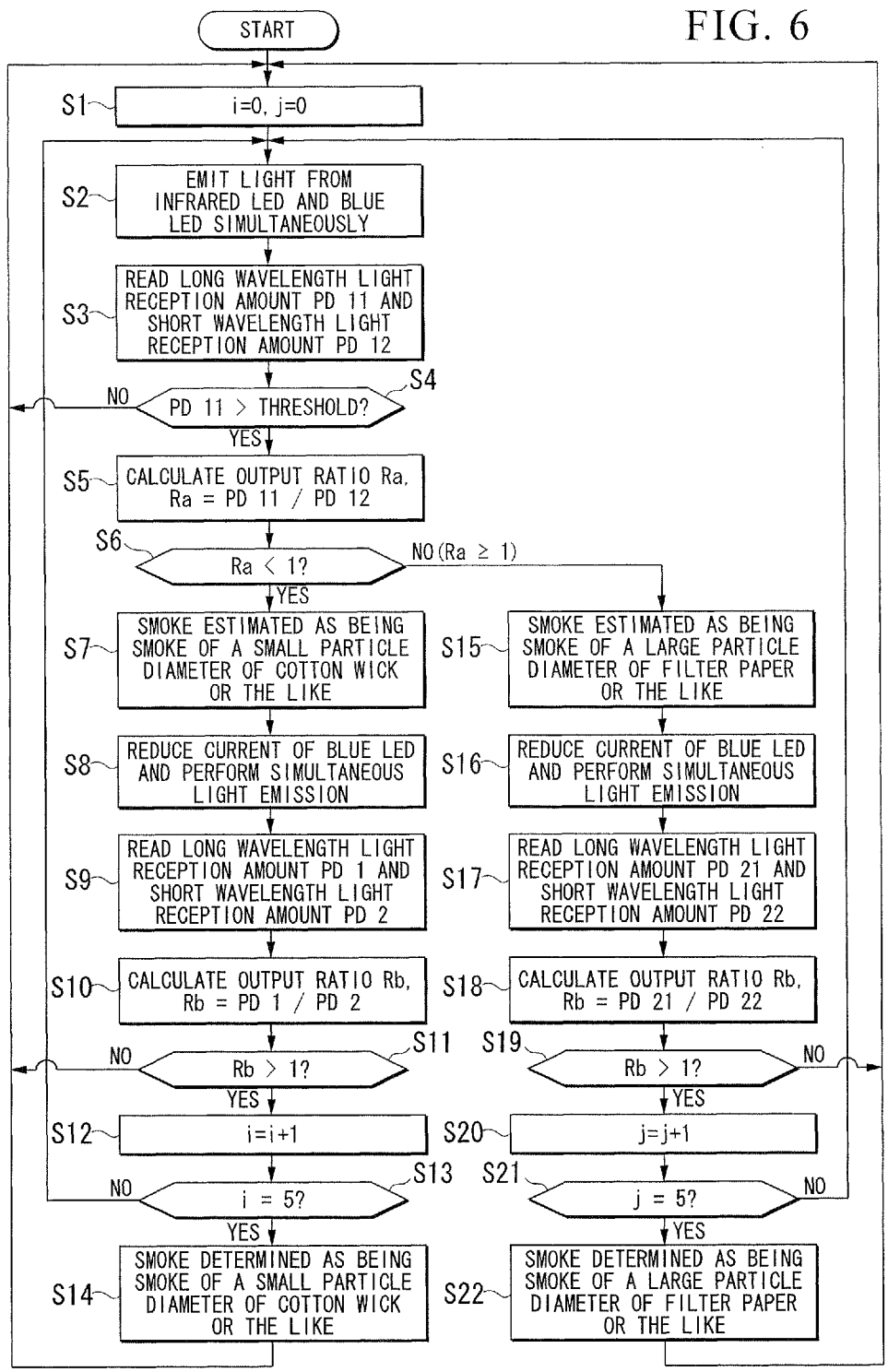
FIG. 6 is a flow chart showing a smoke type determination process performed by a signal processing section shown in FIG. 4 which reduces the light emission current of a blue LED in a re-verification.

FIG. 6 is a flow chart showing a smoke type determination process performed by the signal processing section 28 (refer to FIG. 4) which reduces the light emission current of the blue LED 18 when conducting a re-verification.

As shown in this FIG. 6, first, the counters i and j indicating processing counts are respectively re-set to 0 in step S1, and then in step S2, the infrared LED 14 and the blue LED 18 are made to perform a light emission simultaneously with the same light emission current.

Subsequently, in step S3, the long wavelength light reception amount PD 11 and the short wavelength light reception amount PD 12 obtained by receiving the scattered light due to the simultaneous light emission in step S2 are read.

In the subsequent step S4, it is checked whether or not, for example, the long wavelength light reception amount PD 11 has exceeded a preset threshold value which corresponds to a pre-alarm level indicating a possibility of fire hazard occurrence.

As a result of step S4, if the long wavelength light reception amount PD 11 has exceeded the threshold value corresponding to a pre-alarm level, the process proceeds to step S5, and the output ratio Ra is calculated as Ra=PD 11/PD 12 based on the long wavelength light reception amount PD 11 and the short wavelength light reception amount PD 12 read in step S3.

In the following step S6, it is checked whether or not the calculated output ratio Ra is less than 1. If the result of this is less than 1, then the process proceeds to step S7, and the smoke is estimated as being smoke of a small particle diameter caused by smoking combustion of a cotton wick shown in FIG. 5A. On the other hand, if the output ratio Ra is 1 or higher, the process proceeds to step S15, and the smoke is estimated as being smoke of a large particle diameter caused by smoking combustion of a filter paper or the like shown in FIG. 5B.

Having estimated the smoke type in step S7, the process proceeds to step S8, and the light emission current of the blue LED 18 is reduced for a re-verification and then a simultaneous light emission is performed.

Then, in step S9, as with the step S3, the long wavelength light reception amount PD 21 and the short wavelength light reception amount PD 22 are read.

Subsequently, in step S10, the output ratio Rb is calculated as Rb=PD 1/PD 2.

In the following step S11, it is checked whether or not the output ratio Rb is 1 or higher.

If the result of this is 1 or higher, the process proceeds to step S12, and the counter is set to +1.

In the following step S13, it is checked whether or not i=5, and the process from step S2 is repeated until i=5 has been reached. When i=5 has been reached, the process proceeds to step S14, and the smoke is determined as being smoke with a small particle diameter caused by smoking combustion of a cotton wick or the like. That is to say, in step 14, the estimated result of step S7 is determined as being correct.

On the other hand, also in a case where the output ratio Ra is determined as being 1 or higher in step S6, and the smoke is determined as being smoke of a large particle diameter in step S15, the process of steps S16 to S22 similar to that of steps S7 to S14 is performed. That is to say, similarly, the light emission current of the blue LED 18 is reduced and then a simultaneous light emission is performed, the long wavelength light reception amount PD 21 and the short wavelength light reception amount PD 22 for a re-verification are read, and the output ratio Rb=PD 21/PD 22 is found. Then, if the output ratio Rb is 1 or higher in step S19, the process proceeds to step S20 where the counter j is set to +1, and the process of steps S1 to S6 and S15 to S20 is repeated until the counter j=5 has been reached in step S21. When the counter j=5 has been reached, the process proceeds to step S22, and the smoke is determined as being smoke of a filter paper or the like with a large particle diameter. That is to say, the estimating result of step S15 which estimated the smoke as being smoke with a large particle diameter, is determined as being correct in step S22.

[Second Embodiment]

Hereunder, a second embodiment of a smoke detector of the present invention is described. However, points which differ from those of the above first embodiment are mainly described in the following description.

Figure 7:
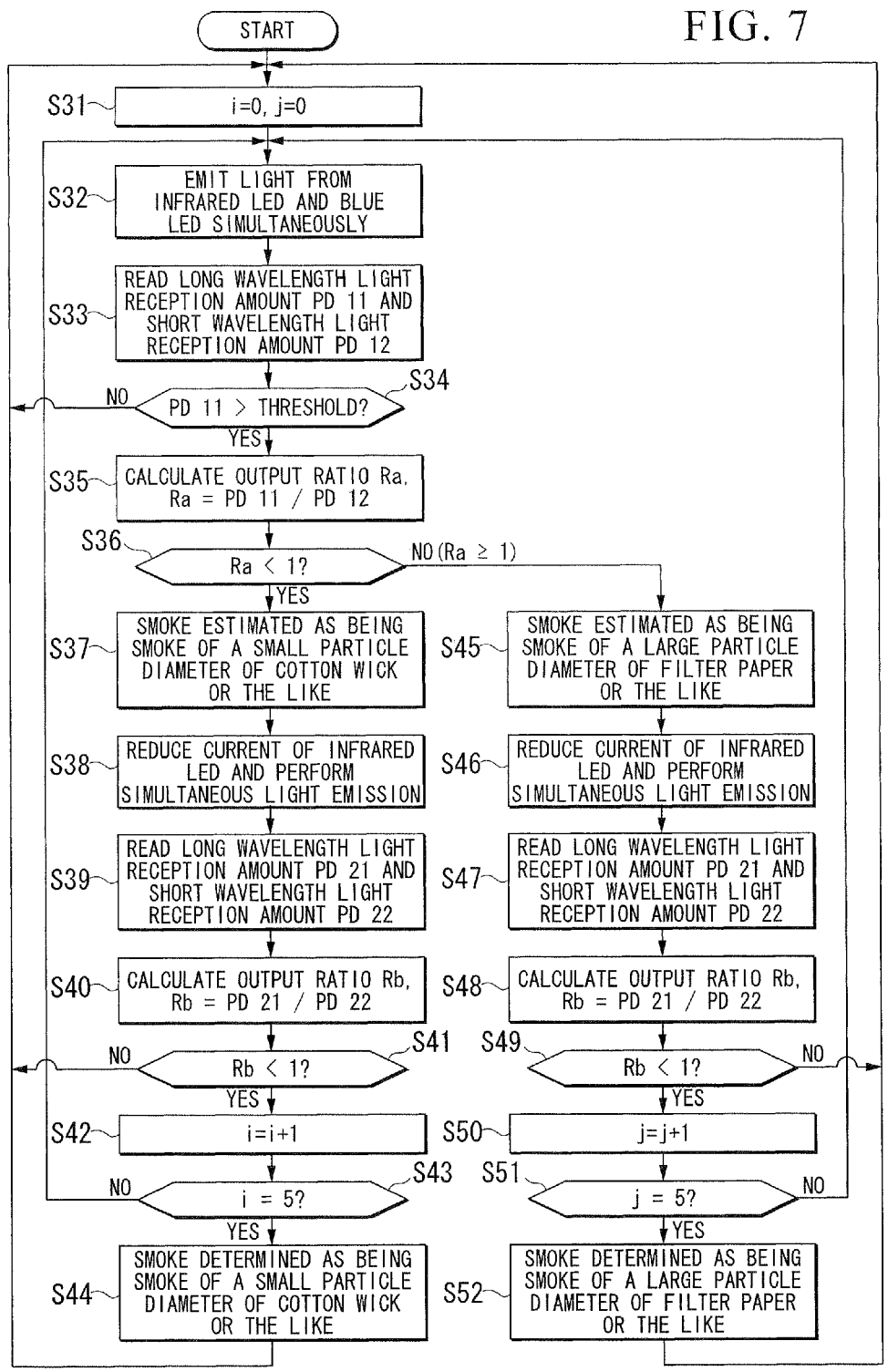
FIG. 7 is a diagram showing a second embodiment of a smoke detector of the present invention, and it is a flow chart showing a smoke type determination process performed by the signal processing section shown in FIG. 4 in the description of the above first embodiment, which reduces the light emission current of an infrared LED in a re-verification.

FIG. 7 is a flow chart showing a smoke type determination process performed by the signal processing section 28 shown in FIG. 4 in the case where the light emission current of the infrared LED 14 is reduced for a re-verification.

Steps S31 to S52 in the process of this FIG. 7 correspond to steps S1 to S22 shown in FIG. 6. However, the process of the present embodiment shown in this FIG. 7 differs from that of the first embodiment in the point that the light emission current of the infrared LED 14, not of the blue LED 18, is reduced and then a simultaneous light emission is performed in steps S38 and S46, and in the point that it judges under a condition where the output ratio Rb found at the time of the re-verification is less than 1.

Specifically, in the process of steps S31 to S44, it is determined whether the condition of the output ratio with the same light emission current shown in FIG. 5A, and the condition of the output ratio Rb in the case where the light emission current of the infrared LED 14 is reduced in the re-verification, are met. In step S44, the estimation in step S37 is determined as being smoke of a small particle diameter caused by smoking combustion of a cotton wick or the like.

Moreover, in the process of steps S31 to S36 and the process of steps S45 to S52, it is determined whether the condition where the output ratio Ra with the same light emission current shown in FIG. 5B is 1 or higher, and the condition where the output ratio Rb in the case of reducing the light emission current of the infrared LED 14 in the re-verification is less than 1, are met. In step S52, the estimation in step S45 is determined as being smoke of a large particle diameter caused by smoking combustion of a filter paper or the like.

The numerical values such as the output ratio mentioned here are illustrated as examples where virtual conditions are set in order to simplify the description, and they may be changed according to the characteristic of each device, the amplification factor of the light receiving section, and other conditions. This similarly applies to the following descriptions.

[Third Embodiment]

Hereunder, a third embodiment of a smoke detector of the present invention is described. However, points which differ from those of the above first embodiment are mainly described in the following description.

Figure 8:
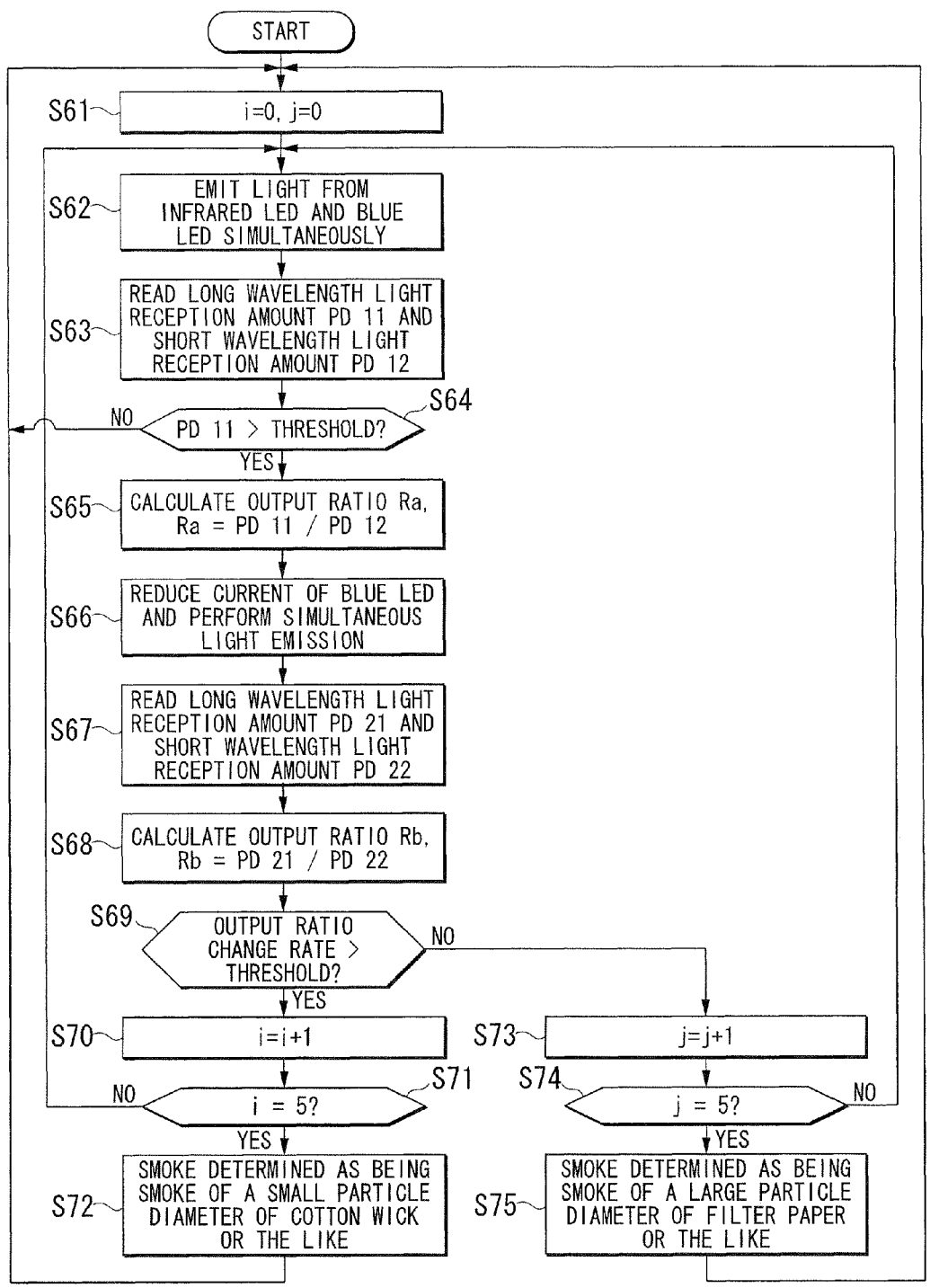
FIG. 8 is a diagram showing a third embodiment of a smoke detector of the present invention, and it is a flow chart showing a smoke type determination process performed by the signal processing section shown in FIG. 4 in the description of the above first embodiment, which determines the output ratio change rate and reduces the light emission current of a blue LED in a re-verification.

FIG. 8 is a flow chart showing a smoke type determination process performed by the signal processing section 28 shown in FIG. 4 in which the output ratio change rate is determined and the light emission current of the blue LED 18 is reduced for a re-verification.

Steps S61 to S68 in this FIG. 8 are the same process as that of steps S1 to S10, excluding steps S6 and S7 shown in FIG. 6. That is to say, the infrared LED 14 and the blue LED 18 are first made to perform light emission simultaneously with the same light emission current, and then the output ratio Ra is calculated, and further, the output ratio Rb at the time when the current of the blue LED 18 is reduced for a re-verification and then a simultaneous light emission is performed, is calculated.

Having found the output ratios Ra and Rb in steps S65 and S68 in this manner, the process proceeds to step S69 where the rate of change from the output ratio Ra to the output ratio Rb is found, and further, it is determined whether or not this change rate is greater than or equal to a threshold value.

Here, as described in FIG. 5A and FIG. 5B, the change rate of the output ratio is as follows.

(1) As for the smoke of a small particle diameter caused by smoking combustion of a cotton wick or the like, in the case where the light emission current of the blue LED 18 is reduced for the re-verification, the rate of change from the output ratio Ra to the output ratio Rb is large.

(2) As for the smoke of a large particle diameter caused by smoking combustion of a filter paper, the rate of change from the output ratio Ra when the light emission current is the same to the output ratio Rb when the light emission current of the blue LED 18 is reduced, is small.

Therefore, in the case where the output ratio change rate is large and is greater than or equal to the threshold value in step S69 in FIG. 8, the process proceeds to step S70 where the counter i is set to +1, and then the process proceeds to step S71. In step S71, the process from steps S62 to S70 is repeated until the counter i=5 has been reached, and when i=5 has been reached, the process proceeds to step S72 where the smoke is determined as being smoke of a small particle diameter caused by smoking combustion of a cotton wick or the like, in accordance with the determination result of (1) above.

On the other hand, in the case where the output ratio change rate is less than the threshold value in step S69, the counter j is set to +1 in step S73, and then, the process proceeds to step S74 and the process from step S62 to S73 is repeated until the counter j=5 has been reached. When the counter j=5 has been reached in step S74, the process proceeds to step S75, and the smoke is determined as being smoke of a large particle diameter caused by smoking combustion of a filter paper or the like, in accordance with (2) above.

[Fourth Embodiment]

Hereunder, a fourth embodiment of a smoke detector of the present invention is described. However, points which differ from those of the above third embodiment are mainly described in the following description.

Figure 9:
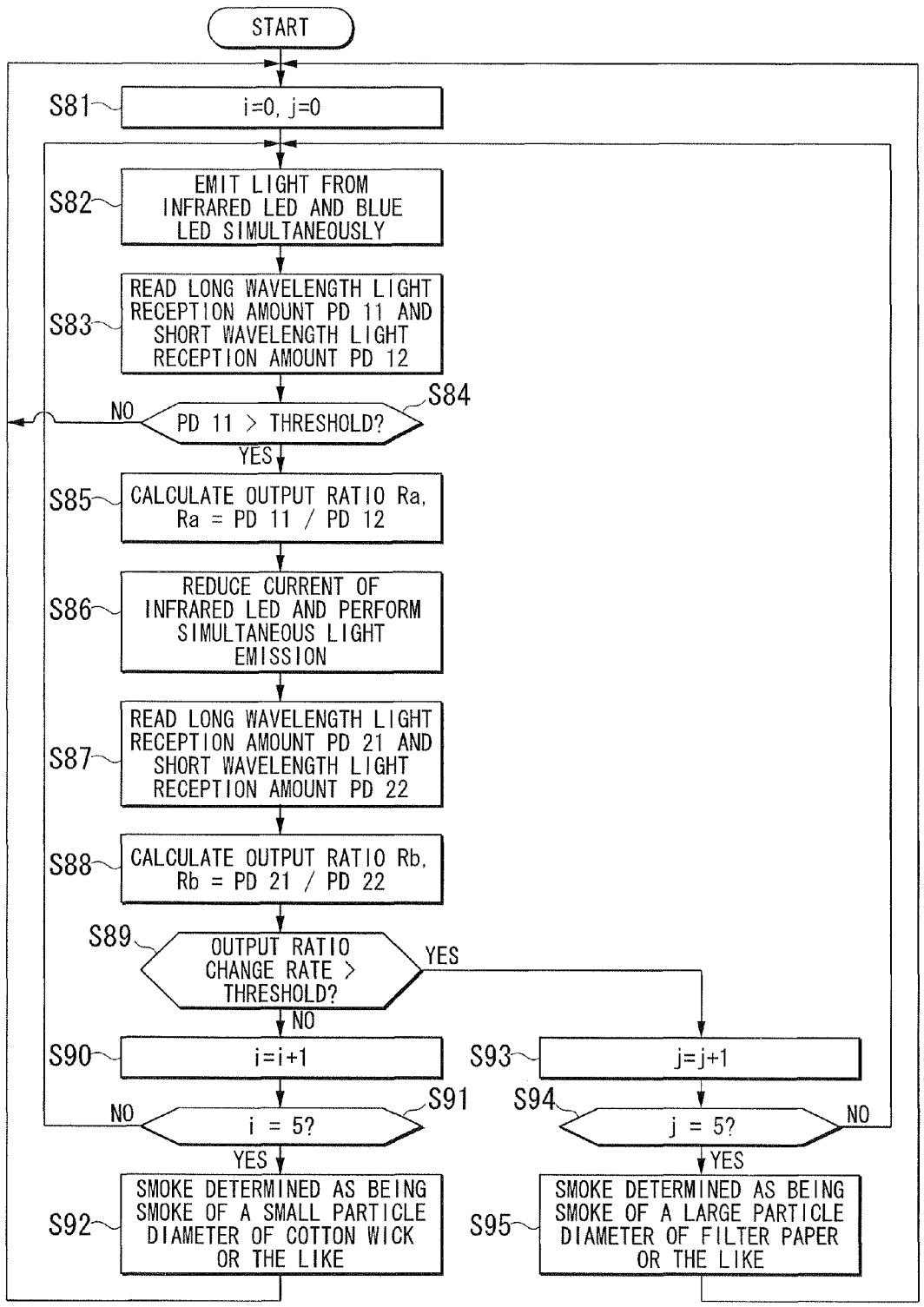
FIG. 9 is a diagram showing a fourth embodiment of a smoke detector of the present invention, and it is a flow chart showing a smoke type determination process performed by the signal processing section shown in FIG. 4 in the description of the above first embodiment, which determines the output ratio change rate and reduces the light emission current of an infrared LED in a re-verification.

FIG. 9 is a flow chart showing a smoke type determination process performed by the signal processing section 28 shown in FIG. 4 in which the output ratio change rate is determined and the light emission current of the infrared LED 14 is reduced for a re-verification.

The process of steps S81 to S95 in FIG. 9 corresponds to the process of steps S61 to S75 shown in FIG. 8. However, the present embodiment differs from the above third embodiment in the point that the light emission current of the infrared LED 14, not of the blue LED 18, is reduced and then a simultaneous light emission is performed when conducting a re-verification in step S86, and in the point of the process of comparing with the threshold value of the change rate from the output ratio Ra to the output ratio Rb in step S89.

In the case shown in FIG. 9 where the light emission current of the infrared LED 14 is reduced when conducting a re-verification, it can be determined as follows, based on the relationship with the output ratio Rb when the light emission current of the infrared LED 14 is reduced at the time of the re-verification shown in FIG. 5A and FIG. 5B.

(1) As for the smoke of a small particle diameter caused by smoking combustion of a cotton wick or the like, the change rate from the output ratio Ra when the light emission current is the same, to the output ratio Rb when the light emission current of the infrared LED 14 is reduced, is small.

(2) As for the smoke of a large particle diameter such as smoke and water vapor caused by smoking combustion of a filter paper, the rate of change from the output ratio Ra when the light emission current is the same, to the output ratio Rb when the light emission current of the infrared LED 14 is reduced, is large.

Therefore, in step S89 of FIG. 9, it is determined whether or not the rate of output change from the output ratio Ra of step S85 found where the light emission current is the same, to the output ratio Rb calculated in step S88 found when the light emission current of the infrared LED 14 is reduced and then a simultaneous light emission is performed in step S86, is greater than or equal to the threshold value. As a result, in the case where the rate of output change is less than the threshold value, the condition of (1) above is taken as being met, and the process proceeds to step S90 where the counter i is set to +1. Furthermore, having repeated the process from step S82 to step S90 until the counter i=5 has been reached in step S91, the process proceeds to step S92, and the smoke is determined as being smoke of a small particle diameter caused by smoking combustion of a cotton wick or the like.

On the other hand, in step S89, in the case where the rate of output change from the output ratio Ra to the output ratio Rb is greater than or equal to the threshold value, the condition of (2) above is taken as being met, and the process proceeds to step S93 where the counter j is set to +1. Furthermore, having repeated the process from step S82 to step S93 until the counter j=5 has been reached in step S94, the process proceeds to step S95, and the smoke is determined as being smoke of a large particle diameter such as smoke caused by smoking combustion of a filter paper.

As described above, in determining the type of smoke based on the rate of output change shown in FIG. 8 of the third embodiment and FIG. 9 of the fourth embodiment, it is possible to perform the comparing process more easily compared to the case shown in FIG. 6 and FIG. 7 where the smoke type is determined by comparing and determining if the output ratios Ra and Rb are 1 or greater or less than 1.

[Fifth Embodiment]

Hereunder, a fifth embodiment of a smoke detector of the present invention is described. However, points which differ from those of the above first embodiment are mainly described in the following description.

Figure 10:
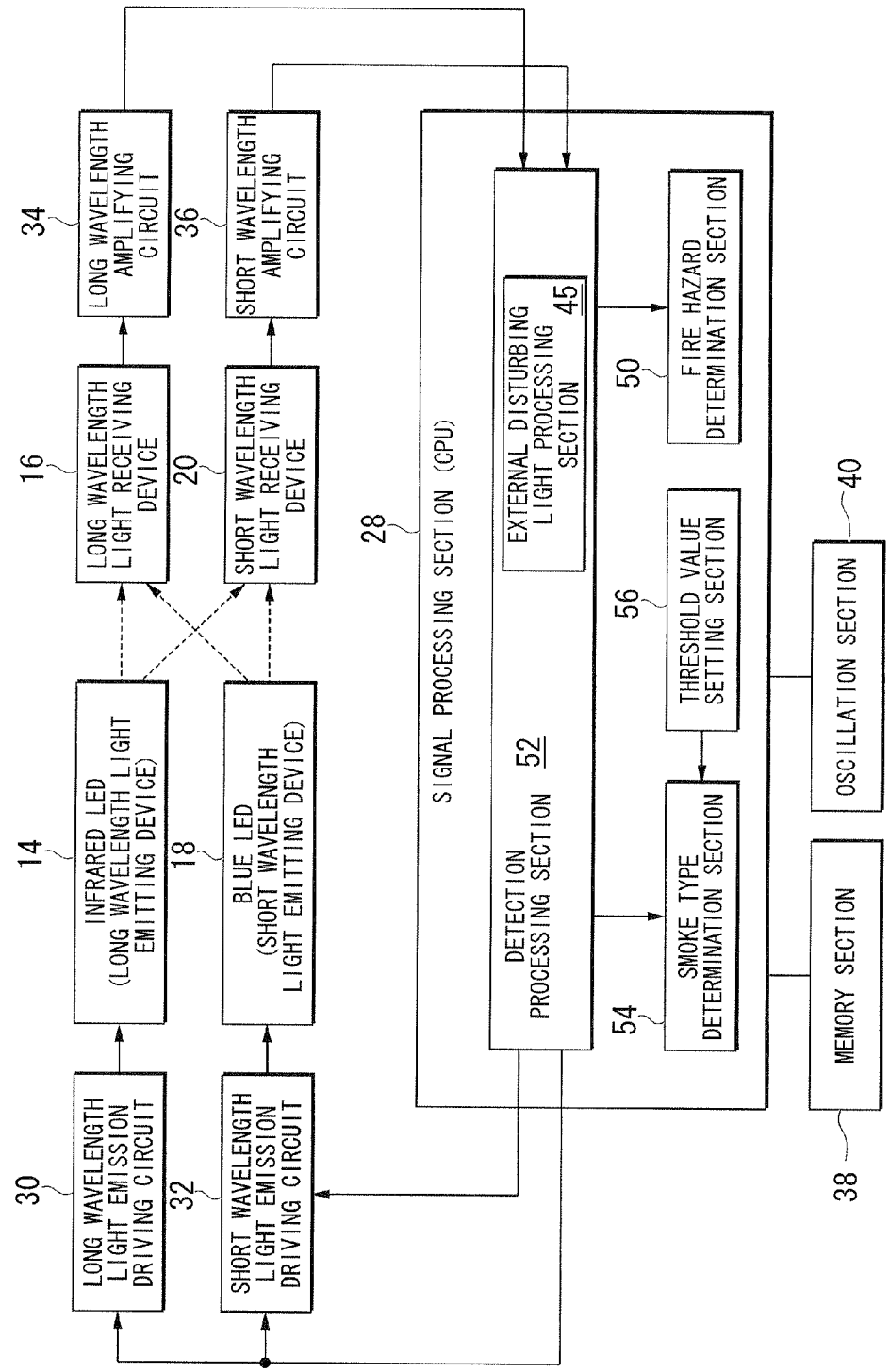
FIG. 10 is a diagram showing a fifth embodiment of a smoke detector of the present invention, and it is a block diagram of a sensor circuit which determines smoke type without performing a re-verification.

FIG. 10 is a block diagram of the present embodiment for determining the type of smoke without conducting a re-verification. As shown in FIG. 10, a sensor circuit of the present embodiment is provided with a signal processing section 28 which uses a CPU, and to this signal processing section 28, as with the first embodiment shown in FIG. 4, there are connected a long wavelength light driving circuit 30, a short wavelength light driving circuit 32, a long wavelength amplifying circuit 34, a short wavelength amplifying circuit 36, a memory section 38, and an oscillation section 40.

The long wavelength light driving circuit 30 and the short wavelength light driving circuit 32 drive respectively an infrared LED 14 and a blue LED 18 to emit light. Moreover, the long wavelength amplifying circuit 34 and the short wavelength amplifying circuit 36 amplify light reception signals from a long wavelength light receiving device 16 and a short wavelength light receiving device 20, and output a long wavelength light reception signal PD 1 and a short wavelength light reception signal PD 2 to the signal processing section 28.

In the signal processing section 28, as functions to be realized by programs executed by the CPU, there are provided a detection processing section 52, a smoke type determination section 54, a threshold value setting section 56, and a fire hazard determination section 50.

The detection processing section 52 makes the infrared LED 14 and the blue LED 18 emit light simultaneously with the same light emission current, and it obtains a long wavelength light reception signal PD 1 and short wavelength light reception signal PD 2 which are obtained in the long wavelength amplifying circuit 34 and the short wavelength amplifying circuit 36 by amplifying the light reception signals from the respective long wavelength light receiving device 16 and the short wavelength light receiving device 20. The smoke type determination section 54 determines the type of smoke based on the long wavelength light reception signal PD 1 and the short wavelength light reception signal PD 2.

The smoke type determination section 54 has the output ratio of the long wavelength light reception signal and the short wavelength light reception signal obtained for one or more preliminarily known smoke types, set in the threshold value setting section 56. Furthermore, based on the setting of the threshold value, the smoke type determination section 54 calculates an output ratio Ra=PD 1/PD 2 between the long wavelength light reception signal PD 1 and the short wavelength light reception signal PD 2 obtained in the detection processing section 52 for the unknown smoke, and compares it with the threshold value set by the threshold value setting section 56, to thereby determine the type of the smoke.

Figure 11A:
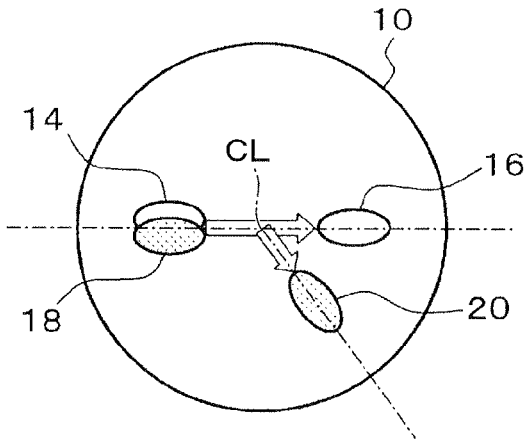
FIG. 11A is an explanatory diagram showing a scattered light detection structure in a case where the position arrangement of a blue LED is displaced with respect to an infrared LED in the same embodiment.
Figure 11B:
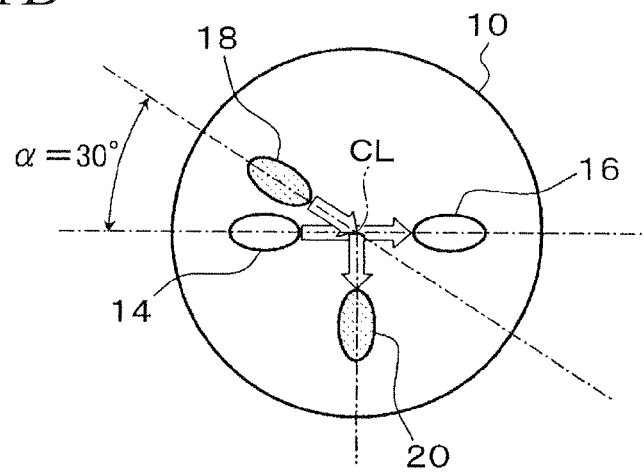
FIG. 11B is an explanatory diagram showing another scattered light detection structure in a case where the position arrangement of the blue LED is displaced with respect to the infrared LED in the same embodiment.
Figure 11C:
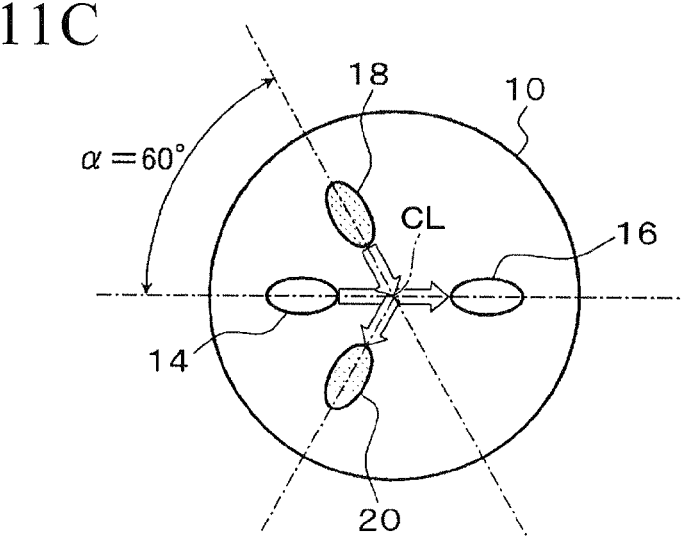
FIG. 11C is an explanatory diagram showing still another scattered light detection structure in a case where the position arrangement of the blue LED is displaced with respect to the infrared LED in the same embodiment.

FIG. 11A to FIG. 11C show a scattered light detection structure in the case where the relative positional arrangement of the blue LED 18 with respect to the infrared LED 14 is displaced in the present embodiment.

FIG. 11A shows a case where in the structure which is provided with a first scattered light detection section provided with the infrared LED 14 and the long wavelength light receiving device 16, and with a second scattered light detection section provided with the blue LED 18 and the short wavelength light receiving device 20, the infrared LED 14 and the blue LED 18 on the light emission side are arranged in approximately the same position.

Where a scattering angle θ1 in the first scattered light detection section is set to θ1=40°, the light reception output based on the scattered light component generated due to the light beam of a long wavelength impinging on smoke particles, becomes prominently greater. Moreover, where a scattering angle θ2 in the second scattered light detection section is set to θ2=90°, which is greater than θ1, the light reception output based on the scattered light component generated due to the light beam of a short wavelength impinging on the smoke particles, hardly receives the influence of the light beam of the long wavelength.

FIG. 11B shows a scattered light detection structure in which the arrangement of the infrared LED 14 is fixed while the blue LED 18 is displaced with respect to this infrared LED 14 by a displacement angle α=30° in a clockwise direction on the horizontal plane (in a clockwise direction about the center axis CL).

FIG. 11C shows a scattered light detection structure in which the blue LED 18 is displaced with respect to the infrared LED 14 by a displacement angle α=60° in a clockwise direction on the horizontal plane (in a clockwise direction about the center axis CL).

As for the different scattered light detection structures with the displacement angles α=0°, 30°, and 60° shown in these FIG. 11A to FIG. 11C, FIG. 12 shows results of measuring the output ratio PD 2/PD 1 in the cases where smoke of a large particle diameter caused by smoking combustion of a filter paper, and smoke of a small particle diameter caused by smoking combustion of a cotton wick, are detected.

In FIG. 12, in the case where the light emitting device displacement angle is α=0°, the output ratio PD 2/PD 1 in the case of filter paper is 0.1 while the output ratio PD 2/PD 1 in the case of cotton wick is 0.2, and the proportions of both of the output ratios is 1:2.

In contrast, when the light emitting device displacement angle is α=30°, the output ratio in the case of the filter paper stays 0.1 while the output ratio in the case of the cotton wick increases to 0.26, and the proportions of the output ratios for the filter paper and cotton wick is 1:2.6.

Furthermore, in the case where the light emitting device displacement angle is α=60°, the output ratio in the case of the filter paper slightly increases to 0.12 while the output ratio in the case of the cotton wick significantly increases to 0.44, and the proportions of the output ratios for the filter paper and cotton wick is 1:3.7.

In the present embodiment shown in FIG. 10, the output ratio for the known smoke shown in FIG. 12 is used as a threshold value, to thereby determine the type of unknown smoke.

Figure 13:
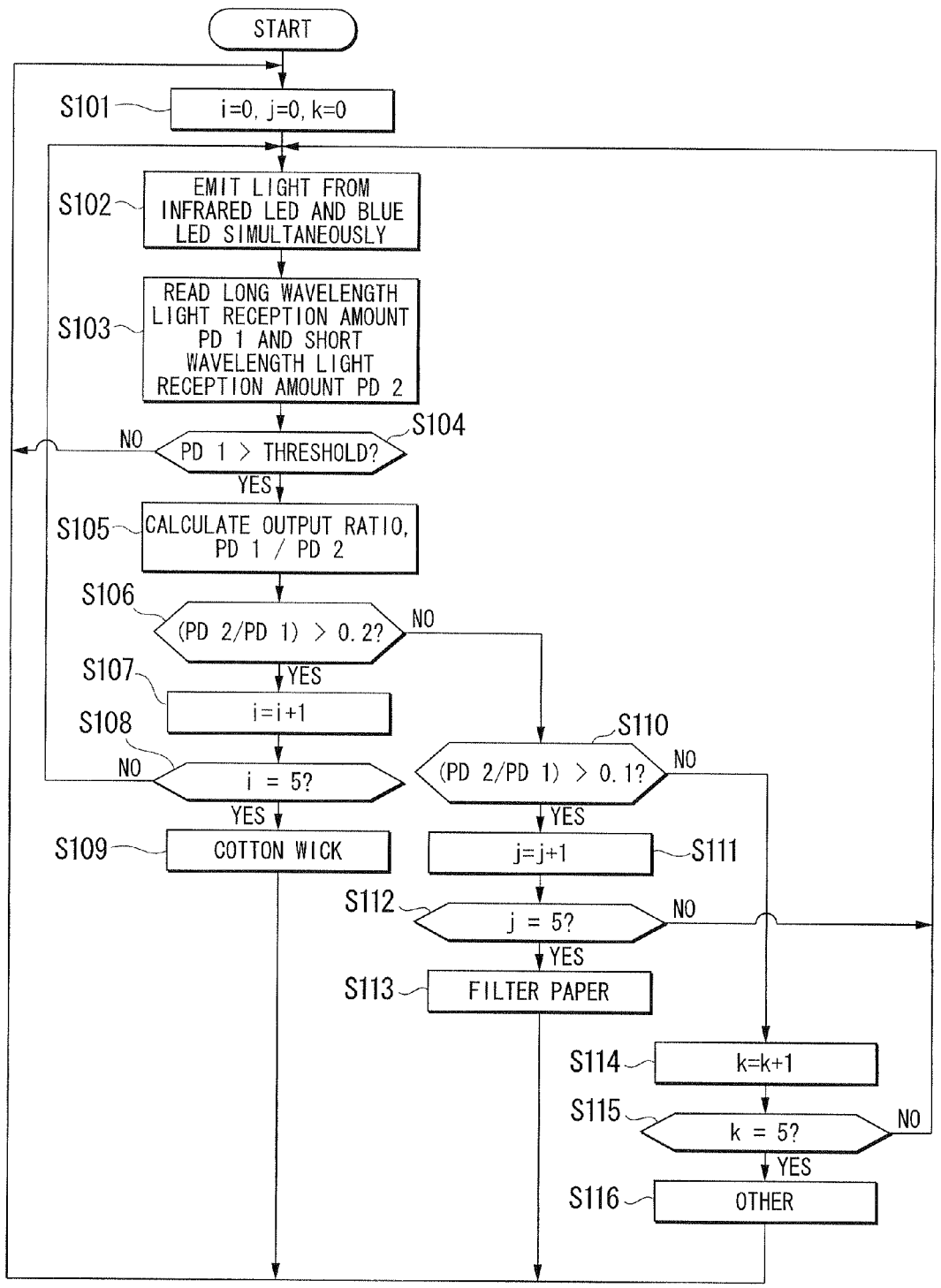
FIG. 13 is a flow chart showing a smoke type determination process performed by the signal processing section shown in FIG. 10.

FIG. 13 is a flow chart showing a smoke type determination process performed by the signal processing section 28 shown in FIG. 10 in a case where the output ratio for the filter paper PD 2/PD 1=0.1 and the output ratio for the cotton wick PD 2/PD 1=0.2 shown in FIG. 12 for the light emitting device displacement angle α=0°, are used as threshold values.

As shown in this FIG. 13, first, the counters i, j, and k are respectively re-set to 0 in step S101, and then the process proceeds to step S102 where the infrared LED 14 and the blue LED 18 are made to perform light emission simultaneously with the same light emission current. Then, having read the long wavelength light reception amount PD 1 and the short wavelength light reception amount PD 2 in step S103, the process proceeds to step S104, and then to step S105 under a condition where the long wavelength light reception amount PD 1 is greater than or equal to a threshold value corresponding to a pre-alarm level, to calculate the output ratio PD 1/PD 2.

Subsequently, in step S106, it is compared with the output ratio 0.2 for the cotton wick serving as a threshold value where α=0° shown in FIG. 12, and if it is greater than or equal to 0.2, the process proceeds to step S107 to set the counter i to +1. In step S108, having repeated the process from step S102 to step S107 until the counter i=5 has been reached, in step S109, the smoke is determined as being smoke caused by smoking combustion of a cotton wick.

On the other hand, in the case where the output ratio is less than the threshold value 0.2 in step S106, the process proceeds to step S110 where it is compared with the output ratio 0.1 for the filter paper shown in FIG. 12 when the light emitting device displacement angle is α=0°, and if it is greater than or equal to the threshold value 0.1, the process proceeds to step S111 where the counter j is set to +1. Then, in step S112, the process of steps S102 to S106 and of steps S110 to S112 is repeated until the counter j=5 has been reached. Then, the process proceeds to step S113, and the smoke is determined as being smoke caused by smoking combustion of a filter paper.

In a case where the output ratio is less than the threshold value 0.1 in step S110, the process proceeds to step S114 and the counter k is set to +1. Then, in step S115, the process of steps S101 to S106 and of steps S110 and S114 is repeated until the counter k=5 has been reached. Then, the process proceeds to step S116, and the smoke is determined as being smoke caused by smoking combustion of substance other than a cotton wick and filter paper.

The flow chart of FIG. 13 takes the case where the light emitting device displacement angle is α=0° shown in FIG. 12 as an example. However, also as for the case of α=30° in FIG. 11B and the case of α=60° in FIG. 11C, it is possible to determine the types of smoke respectively in a similar process with use of the threshold value shown in FIG. 12.

In particular, in the case shown in FIG. 11C where α=60°, the proportions of the output ratios of the filter paper and cotton wick is 1:3.7, which is sufficiently large, and if comparative determination is performed with the output ratio for the filter paper and the output ratio for the cotton wick in this case as threshold values, it is possible to more accurately determine whether the type of smoke is smoke caused by smoking combustion of a cotton wick or smoke caused by smoking combustion of a filter paper.

Next, there is described an external disturbing light processing section 45 which is provided respectively in the first detection processing section 42 and the second detection processing section 44 of the signal processing section 28 shown in FIG. 4, and also in the detection section 52 of the signal processing section 28 shown in FIG. 10.

As shown in FIG. 1A to FIG. 2, since the smoke detector of the present embodiment is a flat type detector, which does not have a labyrinth-structured smoke detection space, in those cases where no measures are taken for noise light, there is a possibility that after the installation thereof, a light beam caused by external disturbing light from a fluorescent lamp or the like may be irradiated as a noise light beam onto the long wavelength light receiving device 16 and the short wavelength light receiving device 20, and consequently determination of a fire hazard and the smoke type based on scattered light caused by smoke may give a false operation. In order to prevent a false-determination of the smoke type and a fire hazard occurrence caused by this type of noise light, the external disturbing light processing section 45 performs a process of suppressing and removing the influence of the noise light contained in the long wavelength light reception signal and the short wavelength light reception signal.

Figure 14:
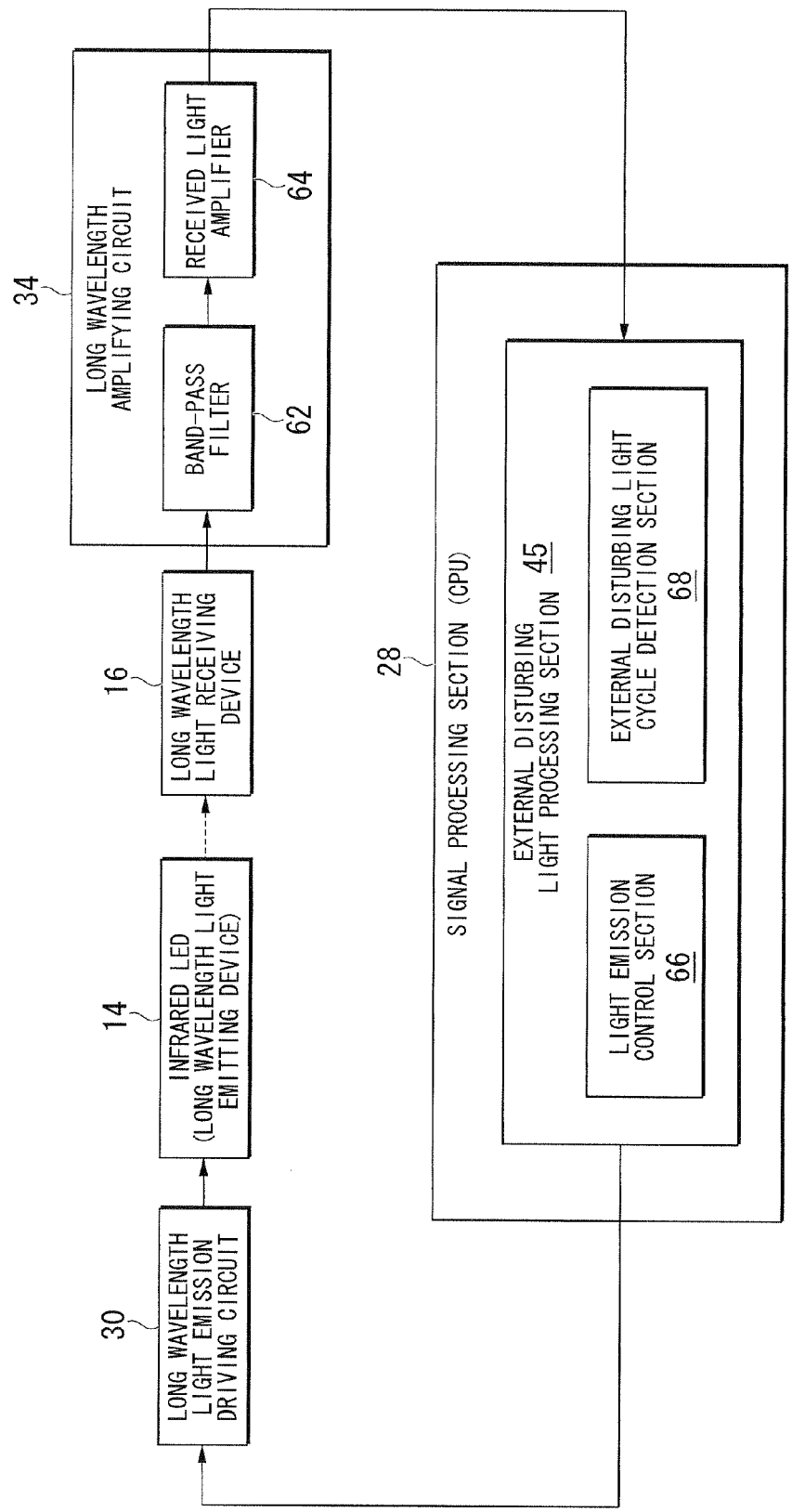
FIG. 14 is a block diagram of an external disturbing light processing section provided in the signal processing section of the present embodiment.

FIG. 14 is a block diagram showing a function configuration of the external disturbing light processing section 45 provided in the signal processing section 28 shown in FIG. 4 and FIG. 10, with an example of the first scattered light detection section provided with the infrared LED 14 and the long wavelength light receiving device 16.

As shown in this FIG. 14, in the signal processing section which uses a CPU, there is provided an external disturbing light processing section 45. In this external disturbing light processing section 45, as functions to be realized by programs executed by the CPU, there are provided a light emission control section 66 and an external disturbing light cycle detection section 68.

Upon receiving a light emission control instruction from the light emission control section 66 provided in the signal processing section 28, the long wavelength light emission driving circuit 30 repeats a process of driving the infrared LED 14 to emit light a predetermined number of times (for example, five times) at a predetermined light emission frequency f1 (for example, f1=3 kHz) in each predetermined light emission cycle T11.

The smoke scattered light obtained as a result of driving the infrared LED 14 to emit light is received by the long wavelength light receiving device 16, and is converted into an electrical signal. In the long wavelength amplifying circuit 34 there are provided a band-pass filter 62 and a received light amplifier 64.

The band-pass filter 62 has a passing frequency band with a light emission driving frequency f1 of the long wavelength light emission driving circuit 30 serving as the center frequency thereof, and it allows light reception signals according to the light emission frequency to pass therethrough and inputs them to the received light amplifier 64.

The received light amplifier 64 amplifies weak light reception signals from the long wavelength light receiving device 16, and outputs them to the signal processing section 28. The signal processing section 28 is provided with an AD-conversion section (not shown in the figure) which converts light reception outputs from the received light amplifier 64 into digital data.

The light emission control section 66 provided in the signal processing section 28 performs control for driving the infrared LED 14 to emit light with respect to the long wavelength light emission driving control circuit 30 a predetermined number of light emissions (for example, five times) at the light emission frequency f1.

During the period of a light emission cycle where the infrared LED 14 is not light emission-driven by the long wavelength light emission driving circuit 30, the external disturbing light cycle detection section 68 detects a cycle S1 of external disturbing light based on the light reception signal from the received light amplifier 64.

The external disturbing light cycle S1 detected by the external disturbing light cycle detection section 68 is read into the light emission control section 66. The light emission control section 66 performs a light emission control which changes the start timing of the light emission cycle to a timing which excludes the detected external disturbing light cycle, thereby preventing external disturbing light caused by noise of a fluorescent lamp or the like from overlapping with the light emission of the infrared LED 14 and preventing this from causing a false report.

Figure 15:
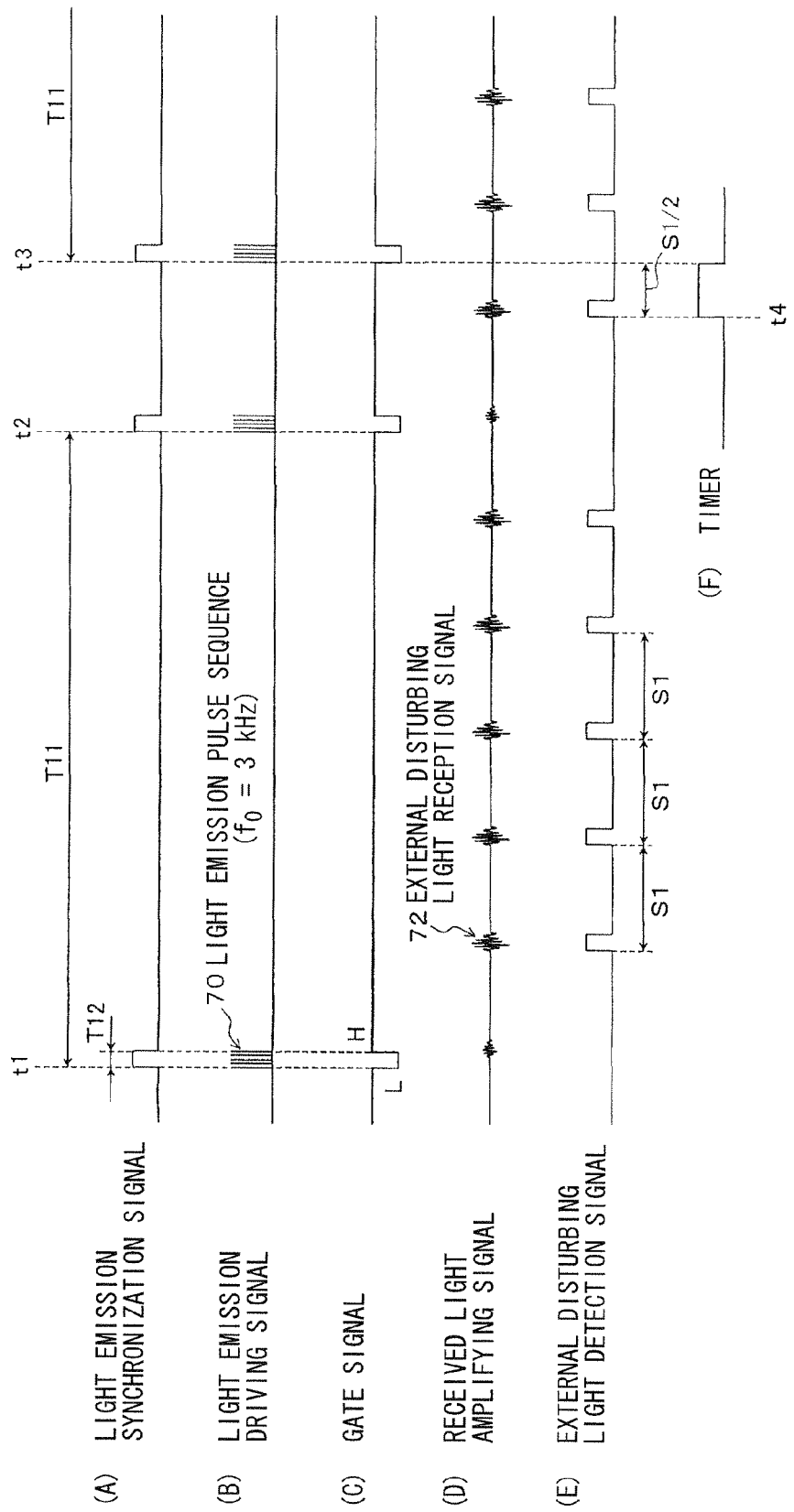
FIG. 15 is a time chart showing a light emission operation and light receiving operation performed by the same external disturbing light processing section.

FIG. 15 is a time chart showing a light emission operation and light receiving operation performed by the external disturbing light processing section 46 shown in FIG. 14. (A) of FIG. 15 shows light emission synchronization signals generated in the light emission control section 66 provided in the signal processing section 28 shown in FIG. 14, and the long wavelength light emission driving circuit 30 is driven for a predetermined light emission period T12 in each light emission cycle T11.

(B) of FIG. 15 shows light emission driving signals output from the long wavelength light emission driving circuit 30 to the infrared LED 14. As shown in (B) of this FIG. 15, in synchronization with the light emission period T12 of light emission synchronization signal, five light emission pulses at light emission frequency f1=3 kHz are output as a light emission pulse sequence 70, making the infrared LED 14 perform pulse light emission five times.

(C) of FIG. 15 shows gate signals. As shown in (C) of this FIG. 15, the gate signal is at L (low) level during the light emission period of the light emission synchronization signal shown in (A) of FIG. 15, and it is at H (high) level during the period where light emission is stopped. Accordingly, these gate signals are used as signals for making a distinction between the light emission period and the light emission stop period in the light receiving process.

(D) of FIG. 15 illustrates the output of the received light amplifier 64 and shows received light amplifying signals at the time of normal operation where there is no smoke flows caused by a fire hazard, and during the light emission stop period within the light emission cycle T11, an external disturbing light reception signal 72 is cyclically output upon receiving external disturbing light caused by an illumination lamp such as fluorescent lamp.

(E) of FIG. 15 shows external disturbing light detection signals which indicate detection of external disturbing light detected with a predetermined threshold value set with respect to the received light amplifying signals shown in (D) of FIG. 15. In the embodiment shown in FIG. 14, an external disturbing light cycle S1 is detected from the external disturbing light detection signals in (E) of FIG. 15, and it sets the start timing of the light emission cycle so as to exclude this external disturbing light cycle S1.

Specifically, during the light emission cycle T11 between times t1 and t2 of FIG. 15, the external disturbing light cycle S1 is found, for example, as an average value of three detection cycles. When the external disturbing light cycle S1 is detected in this manner, light emission driving is performed at time t2 which is the start position of the next light emission cycle, and then, a timer is started when an external disturbing light detection signal is obtained at a first time t4 of the light emission stop period. Then taking the timing of time t3 when a period of time S1/2, which is a half of the detected external disturbing light cycle S1, has elapsed as the start timing of the light emission cycle, light emission control is performed in the subsequent light emission cycle T11.

With this type of change in the start timing of the light emission cycle to exclude the external disturbing light cycle S1, it is possible to perform five light emission drivings which correspond to the light emission period T12 in the light emission cycle T11, at timings which do not allow them to overlap with cyclically occurring external disturbing light. Therefore, even if there is detected a fire hazard based on the scattered light generated by smoke flowing into the external smoke detection space 22 as shown in FIG. 1A and FIG. 1B, it is possible to reliably prevent a false report caused by directly received external disturbing light.

Figure 16:
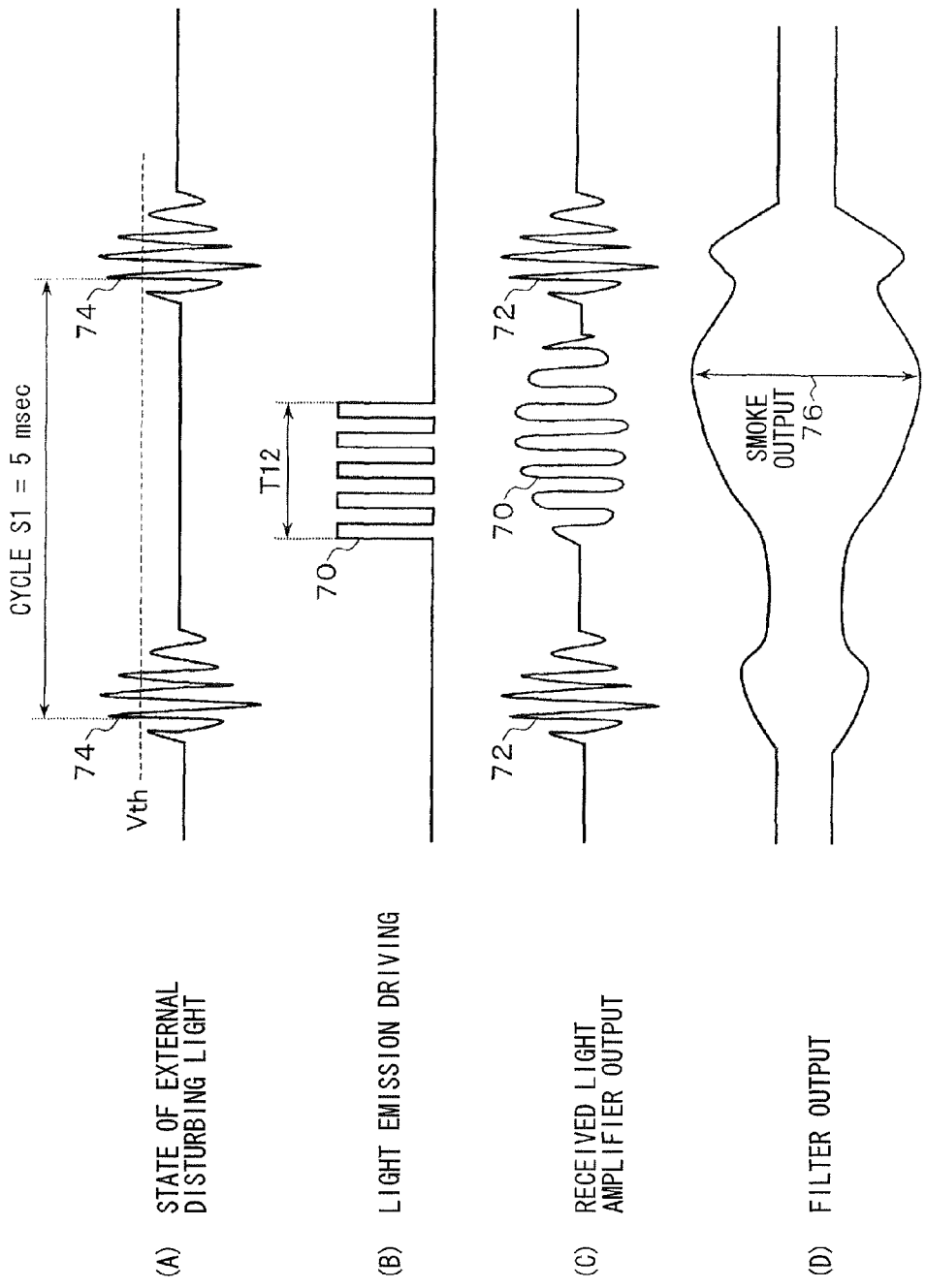
FIG. 16 is a time chart showing a light emission timing setting in a case where an external disturbing light cycle is long.

FIG. 16 is a time chart showing a setting of a light emission start timing in a case where an external disturbing light cycle is long. (A) of FIG. 16 shows the state of external disturbing light. Here, it is assumed that external disturbing light 74 occurs, for example, in a cycle S1=5 msec as shown in (A) of this FIG. 16. By performing light emission driving as shown in (B) of FIG. 16 at the timing in the approximate center of the external disturbing light cycle, with respect to this type of cycle S1 of the external disturbing light 74, it is possible to avoid the external disturbing light 74 and the light emission pulse sequence 70 from overlapping with each other.

Here, the light emission pulse sequence 70 is of a light emission frequency f1=3 kHz, and the cycle per single pulse is approximately 330 μsec. By consecutively outputting this five times, the light emission period T12 becomes T12=2 msec.

(C) of FIG. 16 shows an output of the received light amplifier 64 at the time of obtaining scattered light generated due to external disturbing light and a light beam from the emission driven infrared LED 14 impinging on smoke particles. As shown in (C) of this FIG. 16, since the light emission driving of the light emission pulse sequence 70 is performed while excluding the cycle S1 of the external disturbing light 74, it is input to the received light amplifier output in a state where the external disturbing light reception signal 72 and a smoke light reception signal 70 do not overlap with each other and they can be distinguished from each other.

(D) of FIG. 16 shows a filter output result to illustrate an extracted up/down amplitude component of the received light amplifier shown in (C) of FIG. 16. As for this type of filter output, by reading the filter output of (D) of FIG. 16 at the timing synchronized with the light emission period T12 of the light emitting device shown in (B) of FIG. 16, even if an external disturbing light reception signal is present, it is possible to obtain a smoke output 76 corresponding to the smoke light reception signal to thereby determine a fire hazard and the type of smoke.

Here, the filter output shown in (D) of FIG. 16 can be generated by processing AD-conversion data of the received light amplifier output signal of (C) of FIG. 16 in the AD-conversion section (not shown in the figure) provided in the signal processing section 28 shown in FIG. 14. For example, the smoke light reception signal contained in the received light amplifier output may be AD-converted and read in synchronization with the light emission period T12, and the smoke output 76 may be found as a difference between the minimum value and the maximum value of the AD-converted data. Alternatively, an upper peak and lower peak may be found in data which has been AD-converted in synchronization with the light emission period T12, and the smoke output 76 may be found as a difference in the respective average values.

Figure 17:
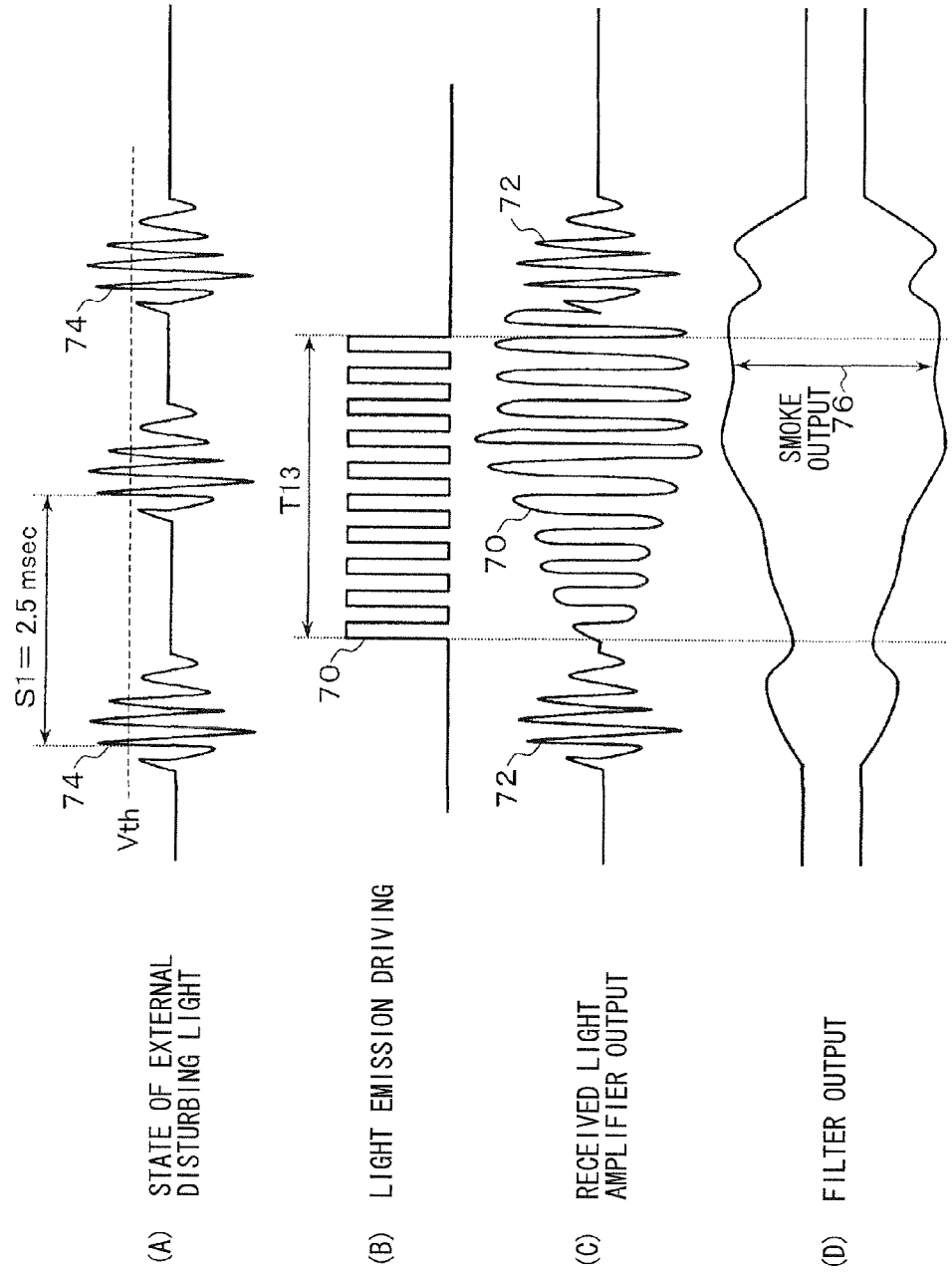
FIG. 17 is a time chart showing an increase in the light emission frequency in a case where an external disturbing light cycle is short.

FIG. 17 is a time chart showing a process performed by the external disturbing light processing section 45 shown in FIG. 14 in a case where the external disturbing light cycle is short. The state of the external disturbing light shown in (A) of FIG. 17 is such that the cycle of the external disturbing light 74 is S1=2.5 msec, which is a half of that in the case of (A) of FIG. 16.

In this type of case where the cycle S1 is short, in a process of driving the light emitting device shown in (B) of FIG. 17, even if the light emission pulse sequence 70 is changed to a timing which excludes the cycle of the external disturbing light 74, the next external disturbing light and the second half portion of the light emission pulse overlap with each other.

Consequently, in the present embodiment, in the case where the cycle S1 of the external disturbing light is shorter than S1=2.5 msec for example, the light emission timing of the light emitting device is changed to a timing which excludes the cycle S1 of the external disturbing light, and at the same time, the number of light emissions is increased from the initially set five times to, for example, ten times, thereby extending the light emission period T13 by twofold to T13=2×T12.

By increasing the light emission pulse sequence 70, for example, from the current frequency of five times to ten times, the next external disturbing light 74 is brought to a state of being embedded in the light emission pulse sequence 70 of the light emission period T13 with the increased number of light emissions. Consequently, by obtaining the smoke output 76 from the difference between the maximum value and the minimum value of the filter output during the light emission period T13 shown in (D) of FIG. 17, which is an amplitude component of the received light amplifier output shown in (C) of FIG. 17 (or from the difference in the average values of the upper peak value and lower peak value), the influence of the external disturbing light can be attenuated. As a result, it is possible to prevent a false report caused by the external disturbing light.

Figure 18:
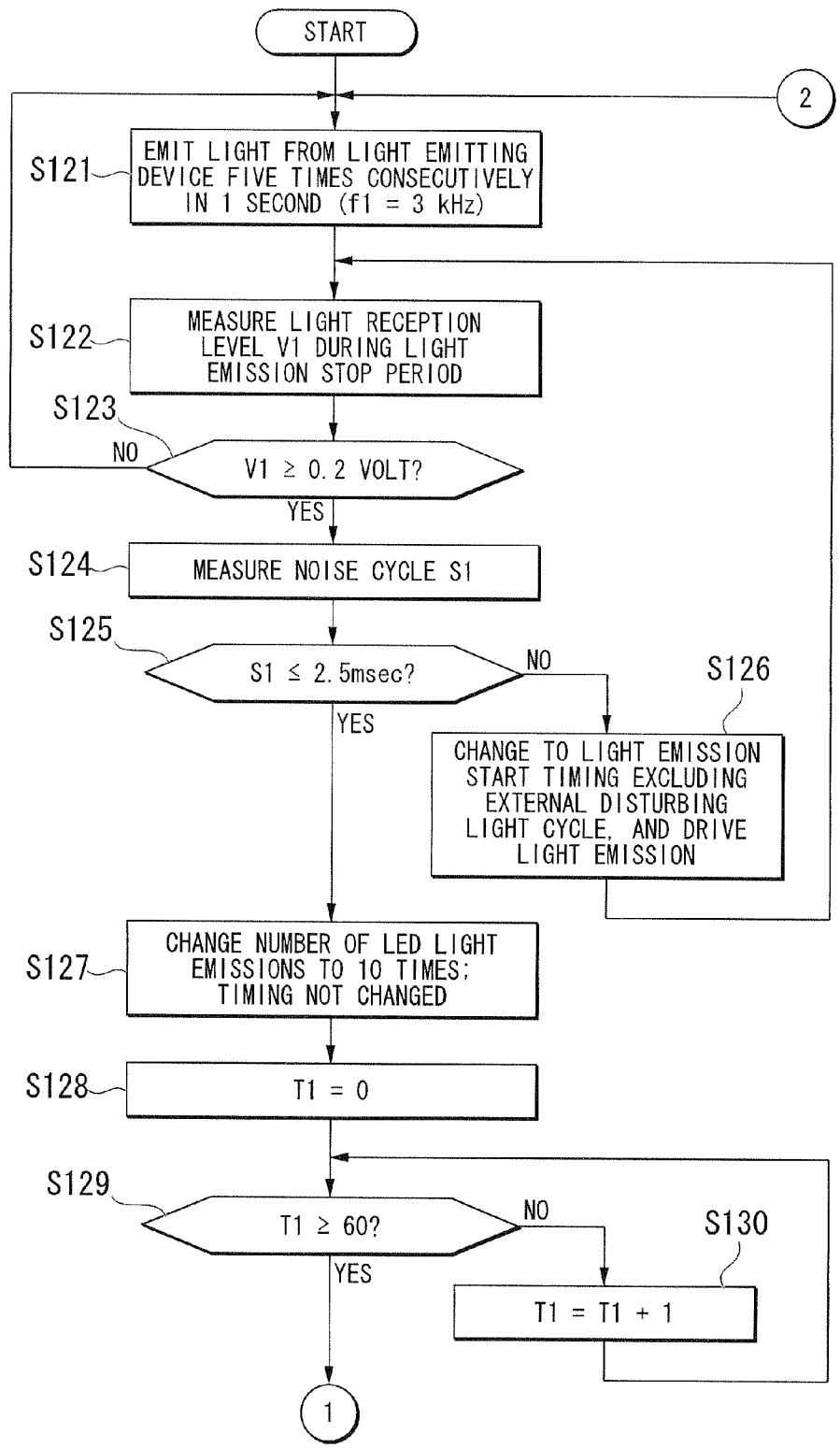
FIG. 18 is a flow chart showing a light emission control process performed by the above external disturbing light processing section.

FIG. 18 is a flow chart showing an external disturbing light process performed by the device shown in FIG. 14, and it shows a control process performed by the light emission control section 66 and the external disturbing light cycle detection section 68 provided in the signal processing section 28.

As shown in FIG. 18, first, in step S121, the infrared LED 14 is made to light five times consecutively, for example, in each light emission cycle T11=1 sec at a light emission frequency f1=3 kHz during the light emission period T12.

Subsequently, in step S122, there is measured a light reception output V1 of the received light amplifier 64 in the light emission stop period where the infrared LED 14 does not emit light. In step S123, if the light reception input level V1 is less than a predetermined threshold value (for example, 0.2 volt), external disturbing light is considered absent, and the process of steps S121 and S122 is repeated.

In step S123, in a case where the light reception input level V1 is greater than or equal to the threshold value 0.2 volt, the external disturbing light is determined as having been received, and the process proceeds to step S124 where the cycle S1 of noise due to the external disturbing light is measured. As shown in (E) of FIG. 15, this noise cycle S1 is measured and found as an average value of noise detection signals, for example, of three cycles obtained from the external disturbing light signal 72 in the light emission stop period.

Next, in step S125, it is checked whether or not the noise cycle S1 is less than or equal to 2.5 msec, and if the noise cycle S1 is long and exceeds 2.5 msec, the process proceeds to step S126. In this step S126, the light emission start timing of the cycle T11 is changed so that the light emitting device is driven to emit light at a timing which excludes the noise cycle, while keeping the number of light emissions to five times, and the process from step S122 is repeated.

On the other hand, if the noise cycle S1 is less than or equal to 2.5 msec in step S125, the process proceeds to step S127, and the number of light emissions of the infrared LED 14 is changed from the current frequency of five times to ten times. In this case, only the number of light emissions is changed from five times to ten times, without changing the start timing of the light emission cycle.

Subsequently, in step S128, having reset the timer T1 to T1=0, the process proceeds to step S129, and it is checked whether or not the timer T1 exceeds a predetermined value 60. If the timer T1 has not exceeded the predetermined value 60, the process proceeds to step S130, and the timer T1 is set to +1. Then, the process repeats to count up the timer T1 in step S130 until the timer T1 has become greater than or equal to 60 in step S129.

Here, where a single count-up time of the timer is 1 sec, the light emission control with the number of light emissions changed to ten times in step S127, is continued until the timer T1 has reached 60 sec in the process of steps S128 to S130.

Figure 19:
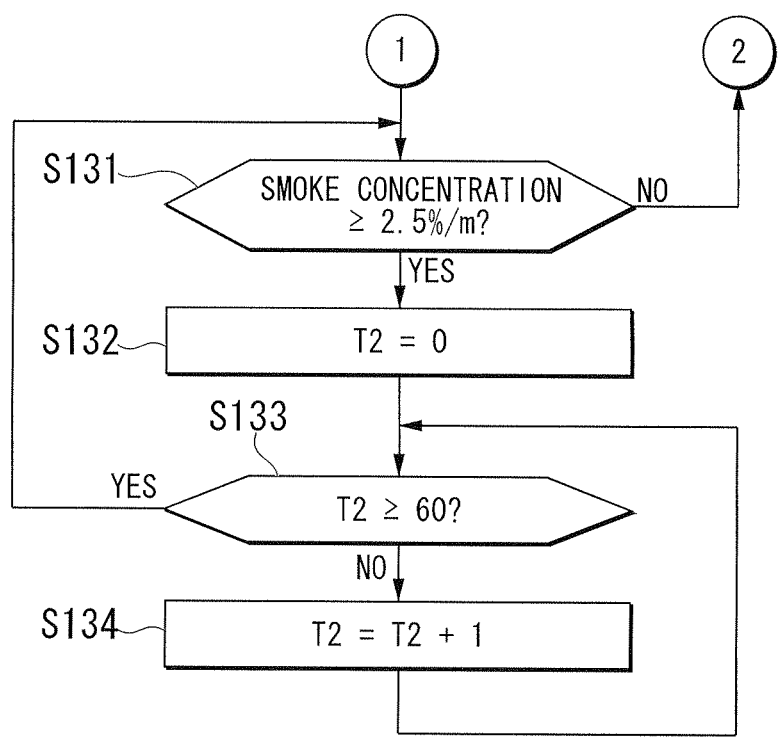
FIG. 19 is a flow chart showing a subsequent process of the light emission control process shown in FIG. 18.

When the timer T1 is determined as having reached 60 sec in step S129, the process proceeds to step S131 shown in FIG. 19, and it is checked whether or not the concentration of smoke is greater than or equal to a smoke concentration 2.5%/m which corresponds to a fire hazard caution level (pre-alarm level). If the smoke concentration is 2.5%/m or higher (that is to say, there is a possibility of smoke caused by a fire hazard), the process proceeds to step S132, and the timer T2 is reset to T2=0. Then, the process proceeds to step S133, and the process of setting the timer T2 to +1 is repeated in step S134 until the timer T2 has become 60 or higher.

Here, where a single count-up time of the timer T2 is 1 sec, in the process of steps S132 to S134, the process returns to step S131 every T2=60 sec, and repeats to check whether or not the smoke concentration has exceeded 2.5%/m.

If the smoke concentration is determined as being less than 2.5%/m in step S132, the process returns to step S121 shown in FIG. 18, and the number of light emissions in the light emission control, which is currently ten times, is reverted to five times. Then, the process of step S122 and thereafter is repeated again.

In the case where the light emitting device cannot be driven to emit light while excluding the external disturbing light cycle because the cycle of the external disturbing light is short, the external disturbing light processing section 45 shown in FIG. 14 increases the number of light emissions of the light emitting device and drives it to emit light beyond the period overlapping with the external disturbing light, to thereby generate a light emission period which does not overlap with the external disturbing light and thus attenuate the degree of influence of the external disturbing light. However, other than this, the following methods may be employed.

(1) In the case where the light emitting device cannot be driven to emit light while excluding the external disturbing light because the cycle of the external disturbing light is too short, the light emission frequency of the light emitting device for performing a predetermined number of light emissions in each light emission cycle, is changed to a light emission frequency which minimizes the level of the external disturbing light influence.

(2) In a case where the light emitting device cannot be driven to emit light while excluding the external disturbing light cycle because the cycle of the external disturbing light is too short, external disturbing light reception signals in the light emission cycle are detected and retained without making the light emitting device emit light, and the external disturbing light component is removed by subtracting the detected and retained external disturbing light signals from the smoke light reception signals obtained in each light emission cycle for performing light emission from the light emitting device.

(3) An external disturbing light receiving device is provided in addition to the smoke light receiving device. Then, having changed the gain of the received light amplifier to correct the external disturbing light reception signal, which has been received and amplified by the external disturbing light receiving device, so that the external disturbing light reception level is matched, the external disturbing light reception signal is subtracted from the smoke light reception signal, which has been received and amplified by the smoke light receiving device, to thereby remove the external disturbing light component.

In the respective embodiments above, a flat type smoke detector which does not have a labyrinth structured smoke detection space in the sensor main body has been described as an example. However, the present invention is not limited to this, and the configuration and method for determining smoke type according to the above respective embodiments may also be applied to a smoke detector of a structure having a labyrinth structured smoke detection space built-into the sensor main body thereof.

Moreover, the above respective embodiments have taken a flat type smoke detector having a flat exposed surface formed therein, however, it does not always have to be flat. The "flat type smoke detector" illustrated here is such that the smoke detection space is not covered with a conventional labyrinth structure and is exposed to the outside, and there is not provided a labyrinth structure therein. Therefore, it may include other configurations which allow a further reduction in the thickness thereof compared to those conventionally practiced. Therefore, the exposed surface may also be of a smooth curved shape for example.

Moreover, the above respective embodiments take a case of detecting smoke caused by a fire hazard as an example. However, it may be utilized not only as a fire hazard sensor but may also be applied to a particle sensor which detects micro particles floating in the air.

The present invention includes appropriate modifications which do not impair the object and advantage thereof, and further, it is not limited by just the numerical values shown in the above embodiments.

INDUSTRIAL APPLICABILITY

According to the smoke detector of the present invention, a light emitting device which emits a light beam of a relatively long wavelength, and a light emitting device which emits a light beam of a relatively short wavelength, are made to perform light emission at the same timing, and it is thereby possible to obtain, with respect to the same smoke, light reception signals of scattered lights created respectively by the long wavelength light beam and the short wavelength light beam. As a result, it is possible to more accurately identify the type of smoke.

DESCRIPTION OF REFERENCE SYMBOLS

- 10 Sensor main body
- 12 Holder
- 14 Infrared LED
- 16 Long wavelength light receiving device
- 18 Blue LED
- 20 Short wavelength light receiving device
- 21a to 21d Opening
- 22 External smoke detection space
- 24 Translucent cover
- 26 Circuit board
- 28 Signal processing section
- 30 Long wavelength light emission driving circuit
- 32 Short wavelength light emission driving circuit
- 34 Long wavelength amplifying circuit
- 36 Short wavelength amplifying circuit
- 38 Memory section
- 40 Oscillation section
- 42 First detection processing section
- 44 Second detection processing section
- 46, 54 Smoke type determination section
- 48, 56 Threshold value setting section
- 50 Fire hazard determination section
- 52 Detection processing section
- 62 Band-pass filter
- 64 Received light amplifier
- 66 Light emission control section
- 68 External disturbing light cycle detection section

The invention claimed is:

1. A smoke detector comprising:
a plurality of light emitting devices which emit light beams of mutually different wavelengths; and
a plurality of scattered light receiving sections which receive, at a different scattering angle for each light beam of the respective wavelength, scattered light generated due to the plurality of light beams emitted simultaneously from these light emitting devices impinging on smoke,
wherein a light emission driving under a first driving condition which makes the plurality of the light emitting devices simultaneously emit light with a light emission current of the same current value, and a light emission driving under a second driving condition which changes a light emission current of at least one of the plurality of the light emitting devices so that the light emission current is different from that of the other light emitting device, are performed at a different timing.

2. The smoke detector according to claim 1, wherein the presence or absence, or type of the smoke is determined based on a correlation between respective light reception signals from each of the scattered light receiving sections.

3. The smoke detector according to claim 1, wherein the presence or absence, or type of the smoke are determined based on a correlation between light reception signals of each of the scattered light receiving sections under the first driving condition, and a correlation between light reception signals of each of the scattered light receiving sections under the second driving condition.

4. A smoke detector comprising:
a first scattered light detection section in which a long wavelength light emitting device which emits a first light beam having a predetermined long wavelength, and a long wavelength light receiving device which receives first scattered light generated due to the first light beam emitted from this long wavelength light emitting device impinging on smoke, are arranged with a first scattering angle;
a second scattered light detection section in which a short wavelength light emitting device which emits a second light beam having a predetermined short wavelength, and a short wavelength light receiving device which receives second scattered light generated due to the second light beam emitted from this short wavelength light emitting device impinging on smoke, are arranged with a second scattering angle, which differs from the first scattering angle;
a light emission control section which makes the long wavelength light emitting device and the short wavelength light emitting device simultaneously perform light emission;
a first detection processing section which obtains a first long wavelength light reception signal from the long wavelength light receiving device, and a first short wavelength light reception signal from the short wavelength light receiving device; and
a second detection processing section which obtains a second long wavelength light reception signal from the long wavelength light receiving device, and a second short wavelength light reception signal from the short wavelength light receiving device,
wherein the light emission control section is provided with a driving current variable control section which changes a driving current of either one of the long wavelength light emitting device and the short wavelength light emitting device so that a driving current of the long wavelength light emitting device and a driving current of the short wavelength light emitting device are different.

5. The smoke detector according to claim 4, further comprising a smoke type determination section which determines the type of the smoke based on the first long wavelength light reception signal, the second long wavelength light reception signal, the first short wavelength light reception signal, and the second short wavelength light reception signal.

6. The smoke detector according to claim 5, wherein:
the light emission control section drives the long wavelength light emitting device and the short wavelength light emitting device to simultaneously perform light emission with the same light emission current;
the first detection processing section obtains the first long wavelength light reception signal from the long wavelength light receiving device and the first short wavelength light reception signal from the short wavelength light receiving device;
the light emission control section changes the light emission current of either one of the long wavelength light emitting device and the short wavelength light emitting device, and then makes them emit light simultaneously;

the second detection processing section obtains the second long wavelength light reception signal from the long wavelength light receiving device and the second short wavelength light reception signal from the short wavelength light receiving device; and the smoke type determination section determines the diameter of particles of the smoke as being greater than a predetermined value if the proportion of a long wavelength light reception signal is relatively higher, or, it determines the diameter of the particles of the smoke as being smaller than the predetermined value if a proportion of a short wavelength light reception signal is relatively higher, based on the first long wavelength light reception signal, the second long wavelength light reception signal, the first short wavelength light reception signal, and the second short wavelength light reception signal.

7. The smoke detector according to either one of claim 6, further comprising a detector main body having a flat exposed surface, wherein:

the long wavelength light emitting device, the long wavelength light receiving device, the short wavelength light emitting device, and the short wavelength light receiving device are respectively embedded in the exposed surface;

the first light beam emitted from the long wavelength light emitting device and the second light beam emitted from the short wavelength light emitting device are irradiated into an external smoke detection space which the exposed surface faces, to thereby generate the first scattered light and the second scattered light generated due to these light beams impinging on the smoke within the external smoke detection space; and the first scattered light is received by the long wavelength light receiving device while the second scattered light is received by the short wavelength light receiving device.

8. The smoke detector according to claim 5, wherein:

the light emission control section makes a light emission current to be flowed to the short wavelength light emitting device lower than a light emission current to be flowed to the long wavelength light emitting device, and makes the short wavelength light emitting device and the long wavelength light emitting device perform a simultaneous light emission;

the second detection processing section obtains the second long wavelength light reception signal from the long wavelength light receiving device, and the second short wavelength light reception signal from the short wavelength light receiving device; and the smoke type determination section (i) finds a first output ratio, which is found by dividing the first long wavelength light reception signal by the second short wavelength light reception signal, (ii) it estimates the diameter of the particles of the smoke as being smaller than a predetermined value if the first output ratio is less than 1, (iii) having established this estimation, it finds a second output ratio, which is found by dividing the second long wavelength light reception signal by the second short wavelength light reception signal, and then (iv) it determines the result of the estimation as being correct if this second output ratio is 1 or higher.

9. The smoke detector according to claim 5, wherein:

the light emission control section makes a light emission current to be flowed to the short wavelength light emitting device lower than a light emission current to be flowed to the long wavelength light emitting device, and makes the short wavelength light emitting device and the long wavelength light emitting device perform a simultaneous light emission;

the second detection processing section obtains the second long wavelength light reception signal from the long wavelength light receiving device, and the second short wavelength light reception signal from the short wavelength light receiving device; and the smoke type determination section (i) finds a first output ratio, which is found by dividing the first long wavelength light reception signal by the first short wavelength light reception signal, (ii) it estimates the diameter of the particles of the smoke as being greater than a predetermined value if this first output ratio is 1 or higher, (iii) having established this estimation, it finds a second output ratio, which is found by dividing the second long wavelength light reception signal by the second short wavelength light reception signal, and then (iv) it determines the result of the estimation as being correct if this second output ratio is 1 or higher.

10. The smoke detector according to claim 5, wherein:

the light emission control section makes a light emission current to be flowed to the short wavelength light emitting device lower than a light emission current to be flowed to the long wavelength light emitting device, and makes the short wavelength light emitting device and the long wavelength light emitting device perform a simultaneous light emission;

the second detection processing section obtains the second long wavelength light reception signal from the long wavelength light receiving device, and the second short wavelength light reception signal from the short wavelength light receiving device; and the smoke type determination section (i) finds a first output ratio, which is found by dividing the first long wavelength light reception signal by the first short wavelength light reception signal, (ii) it estimates the diameter of the particles of the smoke as being smaller than a predetermined value if this first output ratio is less than 1, (iii) having established this estimation, it finds a second output ratio, which is found by dividing the second long wavelength light reception signal by the second short wavelength light reception signal, and then (iv) it determines the result of the estimation as being correct if this second output ratio is less than 1.

11. The smoke detector according to claim 5, wherein:

the light emission control section makes a light emission current to be flowed to the short wavelength light emitting device lower than a light emission current to be flowed to the long wavelength light emitting device, and makes the short wavelength light emitting device and the long wavelength light emitting device perform a simultaneous light emission;

the second detection processing section obtains the second long wavelength light reception signal from the long wavelength light receiving device, and the second short wavelength light reception signal from the short wavelength light receiving device; and the smoke type determination section (i) finds a first output ratio, which is found by dividing the first long wavelength light reception signal by the second short wavelength light reception signal, (ii) it estimates the diameter of the particles of the smoke as being greater than a predetermined value if this first output ratio is 1 or higher, (iii) having established this estimation, it finds a second output ratio, which is found by dividing the second long wavelength light reception signal by the second short wavelength light reception signal, and then (iv) it determines the result of the estimation as being correct if this second output ratio is less than 1.

12. The smoke detector according to claim 5, wherein:
the light emission control section makes a light emission current to be flowed to the short wavelength light emitting device lower than a light emission current to be flowed to the long wavelength light emitting device, and makes the short wavelength light emitting device and the long wavelength light emitting device perform a simultaneous light emission;
the second detection processing section obtains the second long wavelength light reception signal from the long wavelength light receiving device, and the second short wavelength light reception signal from the short wavelength light receiving device; and
the smoke type determination section (i) finds a first output ratio, which is found by dividing the first long wavelength light reception signal by the second short wavelength light reception signal, and a second output ratio, which is found by dividing the second long wavelength light reception signal by the second short wavelength light reception signal, and (ii) it determines the diameter of the particles of the smoke as being smaller than a predetermined value if the rate of change from the first output ratio to the second output ratio is greater than or equal to a predetermined threshold value, or, it determines the diameter of the particles of the smoke as being greater than the predetermined value if the rate of change is less than the threshold value.

13. The smoke detector according to claim 5, wherein:
the light emission control section makes a light emission current to be flowed to the short wavelength light emitting device lower than a light emission current to be flowed to the long wavelength light emitting device, and makes the short wavelength light emitting device and the long wavelength light emitting device perform a simultaneous light emission;
the second detection processing section obtains the second long wavelength light reception signal from the long wavelength light receiving device, and the second short wavelength light reception signal from the short wavelength light receiving device; and
the smoke type determination section (i) finds a first output ratio, which is found by dividing the first long wavelength light reception signal by the second short wavelength light reception signal, and a second output ratio, which is found by dividing the second long wavelength light reception signal by the second short wavelength light reception signal, and (ii) it determines the diameter of the particles of the smoke as being smaller than a predetermined value if the rate of change from the first output ratio to the second output ratio is less than a predetermined threshold value, or, it determines the diameter of the particles of the smoke as being greater than the predetermined value if the rate of change is greater than or equal to the threshold value.

14. A smoke detector comprising:
a first scattered light detection section in which a long wavelength light emitting device which emits a first light beam having a predetermined long wavelength, and a long wavelength light receiving device which receives first scattered light generated due to the first light beam emitted from this long wavelength light emitting device impinging on smoke, are arranged with a first scattering angle;
a second scattered light detection section in which a short wavelength light emitting device which emits a second wavelength light beam having a predetermined short wavelength which is shorter than the long wavelength, and a short wavelength light receiving device which receives second scattered light generated due to the second light beam emitted from this short wavelength light emitting device impinging on smoke, are arranged with a second scattering angle, which differs from the first scattering angle;
a light emission control section which makes the long wavelength light emitting device and the short wavelength light emitting device to simultaneously perform light emission with the same light emission current;
a detection processing section which obtains a long wavelength light reception signal from the long wavelength light receiving device, and a short wavelength light reception signal from the short wavelength light receiving device; and
a smoke type determination section which determines the type of the smoke, based on the long wavelength light reception signal and the short wavelength light reception signal,
wherein the first scattered light detection section and the second scattered light detection section are arranged in order to match a detection point of the first scattered light detection section and a detection point of the second scattered light detection section.

15. The smoke detector according to claim 14, wherein
the smoke type determination section: (i) sets a first output ratio, which is found by dividing a known long wavelength light reception signal obtained with respect to one or more types of preliminarily determined smoke by a known short wavelength light reception signal, as a threshold value; (ii) finds a second output ratio, which is found by dividing the long wavelength light reception signal obtained in the detection processing section with respect to unknown smoke, by the short wavelength light reception signal; and (iii) compares this second output ratio with the threshold value to thereby determined the type of the smoke.

16. The smoke detector according to claim 14, wherein
a position of the short wavelength light emitting device of the second scattered light detection section is arranged so as to be horizontal-rotationally displaced about a predetermined axis, with respect to a position of the long wavelength light emitting device of the first scattered light detection section.

17. The smoke detector according to claim 14, further comprising a detector main body having a flat exposed surface, wherein:
the long wavelength light emitting device, the long wavelength light receiving device, the short wavelength light emitting device, and the short wavelength light receiving device are respectively embedded in the exposed surface;
the first light beam emitted from the long wavelength light emitting device and the second light beam emitted from the short wavelength light emitting device are irradiated into an external smoke detection space which the exposed surface faces, to thereby generate the first scattered light and the second scattered light generated due to these light beams impinging on the smoke within the external smoke detection space; and
the first scattered light is received by the long wavelength light receiving device while the second scattered light is received by the short wavelength light receiving device.

* * * * *